(12) United States Patent
Kim

(10) Patent No.: US 10,115,286 B2
(45) Date of Patent: Oct. 30, 2018

(54) METHOD FOR PROVIDING HEALTH SERVICE AND REFRIGERATOR THEREFOR

(71) Applicant: SAMSUNG ELECTRONICS CO., LTD., Suwon-si (KR)

(72) Inventor: Young Hyun Kim, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 251 days.

(21) Appl. No.: 14/563,612

(22) Filed: Dec. 8, 2014

(65) Prior Publication Data

US 2015/0161871 A1    Jun. 11, 2015

(30) Foreign Application Priority Data

Dec. 6, 2013    (KR) ......................... 10-2013-0151562

(51) Int. Cl.
| | |
|---|---|
| *G05B 23/00* | (2006.01) |
| *G05B 19/00* | (2006.01) |
| *F25B 49/00* | (2006.01) |
| *G06K 9/00* | (2006.01) |
| *G09G 5/02* | (2006.01) |
| *A61B 5/05* | (2006.01) |
| *A61B 5/00* | (2006.01) |
| *A61B 5/02* | (2006.01) |

(Continued)

(52) U.S. Cl.
CPC .......... *G08B 21/18* (2013.01); *A61B 5/02405* (2013.01); *A61B 5/04525* (2013.01); *A61B 5/117* (2013.01); *A61B 5/1171* (2016.02); *A61B 5/4561* (2013.01); *A61B 5/4872* (2013.01); *A61B 5/6887* (2013.01); *A61B 5/7475* (2013.01); *F25D 23/12* (2013.01); *F25D 29/00* (2013.01); *G06F 19/00* (2013.01); *G09B 19/0092* (2013.01); *G16H 40/63* (2018.01); *F25B 2700/02* (2013.01); *F25D 2700/04* (2013.01); *F25D 2700/08* (2013.01)

(58) Field of Classification Search
CPC .............. F25D 2700/08; G06Q 10/087; G06K 2017/0051; G07F 9/026; G07G 1/0045; A61B 5/0006
See application file for complete search history.

(56) References Cited

U.S. PATENT DOCUMENTS

| | | | |
|---|---|---|---|
| 5,410,471 A | 4/1995 | Alyfuku et al. | |
| 5,544,649 A * | 8/1996 | David | A61B 5/6887 128/904 |

(Continued)

FOREIGN PATENT DOCUMENTS

| | | |
|---|---|---|
| EP | 1 021 987 A1 | 7/2000 |
| EP | 1 138 258 A1 | 10/2001 |

(Continued)

*Primary Examiner* — Steven Lim
*Assistant Examiner* — Muhammad Adnan
(74) *Attorney, Agent, or Firm* — Sughrue Mion, PLLC

(57) ABSTRACT

A method of providing a health service through a refrigerator that includes determining biometric information of a user using the refrigerator, searching for a user profile including biometric information corresponding to the determined biometric information from a user profile database stored in the refrigerator, and providing the user with a health service based on a user profile stored in the user profile database corresponding to the user.

16 Claims, 20 Drawing Sheets

(51) Int. Cl.
*A61B 5/08* (2006.01)
*G08B 21/18* (2006.01)
*G09B 19/00* (2006.01)
*A61B 5/1171* (2016.01)
*G16H 40/63* (2018.01)
*A61B 5/024* (2006.01)
*A61B 5/0452* (2006.01)
*A61B 5/117* (2016.01)
*F25D 23/12* (2006.01)
*F25D 29/00* (2006.01)
*G06F 19/00* (2018.01)

(56) References Cited

U.S. PATENT DOCUMENTS

| | | | |
|---|---|---|---|
| 6,906,533 B1* | 6/2005 | Yoshida | A61B 5/0537 324/611 |
| 7,617,058 B2 | 11/2009 | Kim et al. | |
| 8,250,871 B2* | 8/2012 | Kwon | F25D 11/02 236/94 |
| 9,129,451 B2* | 9/2015 | Frueh | G07C 9/00087 |
| 9,323,912 B2* | 4/2016 | Schultz | G06F 21/32 |
| 9,721,175 B2* | 8/2017 | Kursun | G06K 9/00926 |
| 9,778,842 B2* | 10/2017 | Ferren | G06F 3/04886 |
| 9,892,576 B2* | 2/2018 | Kursun | G07C 9/00158 |
| 2005/0080353 A1* | 4/2005 | Whang | A61B 5/0537 600/547 |
| 2005/0151620 A1* | 7/2005 | Neumann | G06K 9/00006 340/5.52 |
| 2005/0194437 A1* | 9/2005 | Dearing | G06K 7/10336 235/382 |
| 2006/0122532 A1 | 6/2006 | Lee et al. | |
| 2006/0183980 A1* | 8/2006 | Yang | A61B 5/6804 600/301 |
| 2006/0217600 A1 | 9/2006 | Lee et al. | |
| 2006/0224050 A1 | 10/2006 | Lee et al. | |
| 2007/0081696 A1* | 4/2007 | Brennan | G07C 9/00158 382/115 |
| 2010/0311482 A1* | 12/2010 | Lange | A61B 5/0404 463/1 |
| 2011/0224505 A1 | 9/2011 | Sadhu | |
| 2012/0189177 A1* | 7/2012 | Oh | G06K 9/228 382/128 |
| 2012/0232903 A1* | 9/2012 | Cenedese | A47L 15/4293 704/246 |
| 2012/0299949 A1* | 11/2012 | Suzuki | G06K 9/00912 345/591 |
| 2013/0002399 A1* | 1/2013 | Frueh | G07C 9/00087 340/5.53 |
| 2014/0046144 A1* | 2/2014 | Jayaraman | A61B 5/165 600/301 |
| 2014/0163335 A1* | 6/2014 | Horseman | G06F 19/3418 600/301 |
| 2014/0211929 A1* | 7/2014 | Krishnan | H04M 3/56 379/142.04 |
| 2014/0218496 A1* | 8/2014 | Park | G06Q 10/10 348/77 |
| 2014/0265759 A1* | 9/2014 | Cloyd | A47B 67/02 312/209 |
| 2014/0281568 A1* | 9/2014 | Ross | G06F 21/32 713/186 |
| 2014/0337949 A1* | 11/2014 | Hoyos | H04L 63/0861 726/7 |
| 2015/0046328 A1* | 2/2015 | Mitra | G06Q 20/40145 705/44 |
| 2015/0260449 A1* | 9/2015 | Furuta | G09B 19/0092 62/125 |

FOREIGN PATENT DOCUMENTS

| | | |
|---|---|---|
| JP | 07-012635 A | 1/1995 |
| JP | 09-119859 A | 5/1997 |
| JP | 11-257714 A | 9/1999 |
| JP | 11-257715 A | 9/1999 |
| JP | 11-347007 A | 12/1999 |
| JP | 2000-083865 A | 3/2000 |
| JP | 2000-107149 A | 4/2000 |
| JP | 2000-107150 A | 4/2000 |
| JP | 2000-126088 A | 5/2000 |
| JP | 2000-126331 A | 5/2000 |
| JP | 2000-152919 A | 6/2000 |
| JP | 2000-225101 A | 8/2000 |
| JP | 2000-225102 A | 8/2000 |
| JP | 2000-229131 A | 8/2000 |
| JP | 2000-287890 A | 10/2000 |
| JP | 2000-316757 A | 11/2000 |
| JP | 2000-333927 A | 12/2000 |
| JP | 2001-000411 A | 1/2001 |
| JP | 2001-029348 A | 2/2001 |
| JP | 2001-037681 A | 2/2001 |
| JP | 2001-054509 A | 2/2001 |
| JP | 2001-321297 A | 11/2001 |
| JP | 2002-224074 A | 8/2002 |
| JP | 2002-224075 A | 8/2002 |
| JP | 2002-224076 A | 8/2002 |
| JP | 2002-224077 A | 8/2002 |
| JP | 2002-242259 A | 8/2002 |
| JP | 2002-330938 A | 11/2002 |
| JP | 2002-330939 A | 11/2002 |
| JP | 2003-220042 A | 8/2003 |
| JP | 2004-254794 A | 9/2004 |
| JP | 2004-344518 A | 12/2004 |
| JP | 2005-102910 A | 4/2005 |
| JP | 2005-218832 A | 8/2005 |
| JP | 2005-291754 A | 10/2005 |
| JP | 2005-291755 A | 10/2005 |
| JP | 2006-17560 A | 1/2006 |
| JP | 2008-083070 A | 4/2008 |
| JP | 2002-263035 A | 9/2008 |
| JP | 2008-234371 A | 10/2008 |
| JP | 2010-230359 A | 10/2010 |
| KR | 1993-0017550 A | 9/1993 |
| KR | 10-2004-0094941 A | 11/2004 |
| KR | 10-2006-0018408 A | 3/2006 |
| KR | 10-2006-0032440 A | 4/2006 |
| KR | 10-2006-0067483 A | 6/2006 |
| KR | 10-2006-0083304 A | 7/2006 |
| KR | 10-2006-0083551 A | 7/2006 |
| KR | 10-2006-0096734 A | 9/2006 |
| KR | 10-0629568 B1 | 9/2006 |
| KR | 10-2006-0110048 A | 10/2006 |
| KR | 10-2006-0117718 A | 11/2006 |
| KR | 10-0645134 B1 | 11/2006 |
| KR | 10-2007-0003238 A | 1/2007 |
| KR | 10-0681595 B1 | 2/2007 |
| KR | 10-2007-0029017 A | 3/2007 |
| KR | 10-2008-0037305 A | 4/2008 |
| KR | 10-2012-0020873 A | 3/2012 |
| KR | 10-1270954 B1 | 6/2013 |

* cited by examiner

| USER | NAME | ELECTRO-CARDIOGRAM | BODY FAT | BODY COMPOSITION | MUSCLE MASS | PACE MAKER | IRIS | FINGER-PRINT | VOICE-PRINT | AGE | SEX | HEIGHT | WEIGHT | SKIN COLOR | EATING HABITS |
|---|---|---|---|---|---|---|---|---|---|---|---|---|---|---|---|
| 1 | A1 | B1 | C1 | D1 | E1 | F1 | G1 | H1 | I1 | J1 | K1 | L1 | M1 | N1 | O1 |
| 2 | A2 | B2 | C2 | D2 | E2 | F2 | G2 | H2 | I2 | J2 | K2 | L2 | M2 | N2 | O2 |
| 3 | A3 | B3 | C3 | D3 | E3 | F3 | G3 | H3 | I3 | J3 | K3 | L3 | M3 | N3 | O3 |

FIG.15

METHOD FOR PROVIDING HEALTH SERVICE AND REFRIGERATOR THEREFOR

CROSS-REFERENCE TO RELATED APPLICATION

This application claims priority under 35 U.S.C. § 119(a) to Korean Application Serial No. 10-2013-0151562, which was filed in the Korean Intellectual Property Office on Dec. 6, 2013, the entire content of which is hereby incorporated by reference.

BACKGROUND

Field

The present disclosure relates to a refrigerator.

Description of Related Art

A refrigerator is a device for keeping food cool and fresh so that the food does not spoil. The refrigerator is categorized based on form and function.

For example, the refrigerator may be a general refrigerator including a fridge and a freezer for various purposes, a kimchi refrigerator, a wine refrigerator, a cosmetic cooler, a portable refrigerator, a refrigerator for vehicles, a rice refrigerator, a side dish refrigerator, and the like. The refrigerator may be a single door refrigerator, a two-door refrigerator, a four-door refrigerator, and the like. The refrigerator may be shared by an entire household, and is an essential device.

Recently, as income and an interest in improving general quality of life have increased, people concerned with a healthy lifestyle desire to receive customized health information and a well-being service including the same. However, it is difficult from the perspective of cost and time.

SUMMARY

Among the constituents of a human body, fat does not let a current flow. Accordingly, for measurement of body fat, a fat component ratio may be estimated based on a body resistance that is measured by letting a current flow through a body and measuring a voltage applied to a device. When parameters including a height, a weight, a sex, and an age of a user are given, a body fat percentage may be determined by inputting the parameters and the measured resistance value into an equation generated in advance.

However, a current of 500 µA and 50 kHz flowing through the body while measuring body fat may disturb the operation of a pacemaker and thus, a person who has a pacemaker may not use the service. When it is not checked, a person with a pacemaker may encounter a serious problem if body fat is measured.

The measurement of body resistance is strongly influenced by a length of a body, and a length and a cross-section area are changed based on a posture of the body. For example a body that is bent or straightened may have a different resistance. The change may be greater than a change in resistance caused by a decrease in body fat and thus, the body fat may be inaccurately measured without taking into consideration the posture of the body.

According to an exemplary embodiment of the present disclosure, a method of providing a health service through a refrigerator is provided. The method includes determining biometric information of a user using the refrigerator, searching for a user profile including biometric information corresponding to the determined biometric information, from a user profile database stored in the refrigerator, and providing the user with a health service based on the user profile.

The determined biometric information may be an electrocardiogram of the user.

The electrocardiogram of the user may be identification information from which a predetermined common component is removed.

The method may further include determining whether to update the user profile, based on a point in time of registration of the information included in the user profile.

The method may further include obtaining biometric information of the user for updating the user profile.

The method may further include including the obtained biometric information in the user profile.

The method may further include determining whether it is appropriate to measure a body resistance of the user, based on the user profile, measuring the body resistance of the user when it is appropriate to measure the body resistance, and determining body fat of the user based on the body resistance.

The method may further include determining whether a posture of the user for measuring the body resistance is appropriate based on an image obtained by photographing the user; and when the posture is inappropriate, providing the user with advice about a predetermined posture.

When the user profile includes information indicating that a pacemaker is used, it may be determined that measuring the body resistance of the user is inappropriate.

The measured biometric information may include facial recognition information of the user, iris recognition information, or fingerprint recognition information.

The method may further include receiving device information of an electronic device adjacent to the refrigerator, wherein the received device information is used for searching for the user profile.

A machine-readable storage medium that records a program for implementing a method of providing a health service through a refrigerator.

According to another aspect of an exemplary embodiment of the present disclosure, a refrigerator that provides a health service is provided. The refrigerator includes a storage unit that stores at least one user profile; a sensor unit that determines biometric information of a user; and a controller that searches for a user profile including biometric information corresponding to the determined biometric information, from the at least one user profile, and provides the user with a health service based on the user profile.

The sensor unit may include an electrocardiogram sensor unit that determines an electrocardiogram of the user using an electrode; and the measured biometric information may be an electrocardiogram of the user.

The controller may search for the user profile using identification information obtained by removing a predetermined common component from the electrocardiogram of the user.

The controller may determine whether to update the retrieved user profile, based on a point in time of registration of the information included in the user profile.

The refrigerator may include a body resistance sensor unit that measures a body resistance of the user; and the controller may determine whether it is appropriate to measure the body resistance of the user based on the retrieved user profile; measure the body resistance of the user using the body resistance sensor unit when it is appropriate to measure the body resistance of the user; and calculate body fat of the user based on the body resistance.

The controller may determine whether a posture of the user for measuring the body resistance is appropriate, based on an image obtained by photographing the user; and provide the user with advice about a predetermined posture when the posture of the user is inappropriate.

When the user profile indicates that a pacemaker is used, the controller may determine that measuring the body resistance of the user is inappropriate.

The sensor unit may include a camera that recognizes a face of the user, an iris sensor that recognizes an iris of the user, a fingerprint sensor that recognizes a fingerprint of the user, or a communication unit that receives, from an electronic device adjacent to the refrigerator, device information of the electronic device.

BRIEF DESCRIPTION OF THE DRAWINGS

The above and/or other aspects will become apparent and more readily appreciated from the following description of exemplary embodiments, taken in conjunction with the accompanying drawings, in which:

FIG. 15 illustrates user profiles according to an exemplary embodiment;

DETAILED DESCRIPTION OF EXEMPLARY EMBODIMENTS

Figure 1:
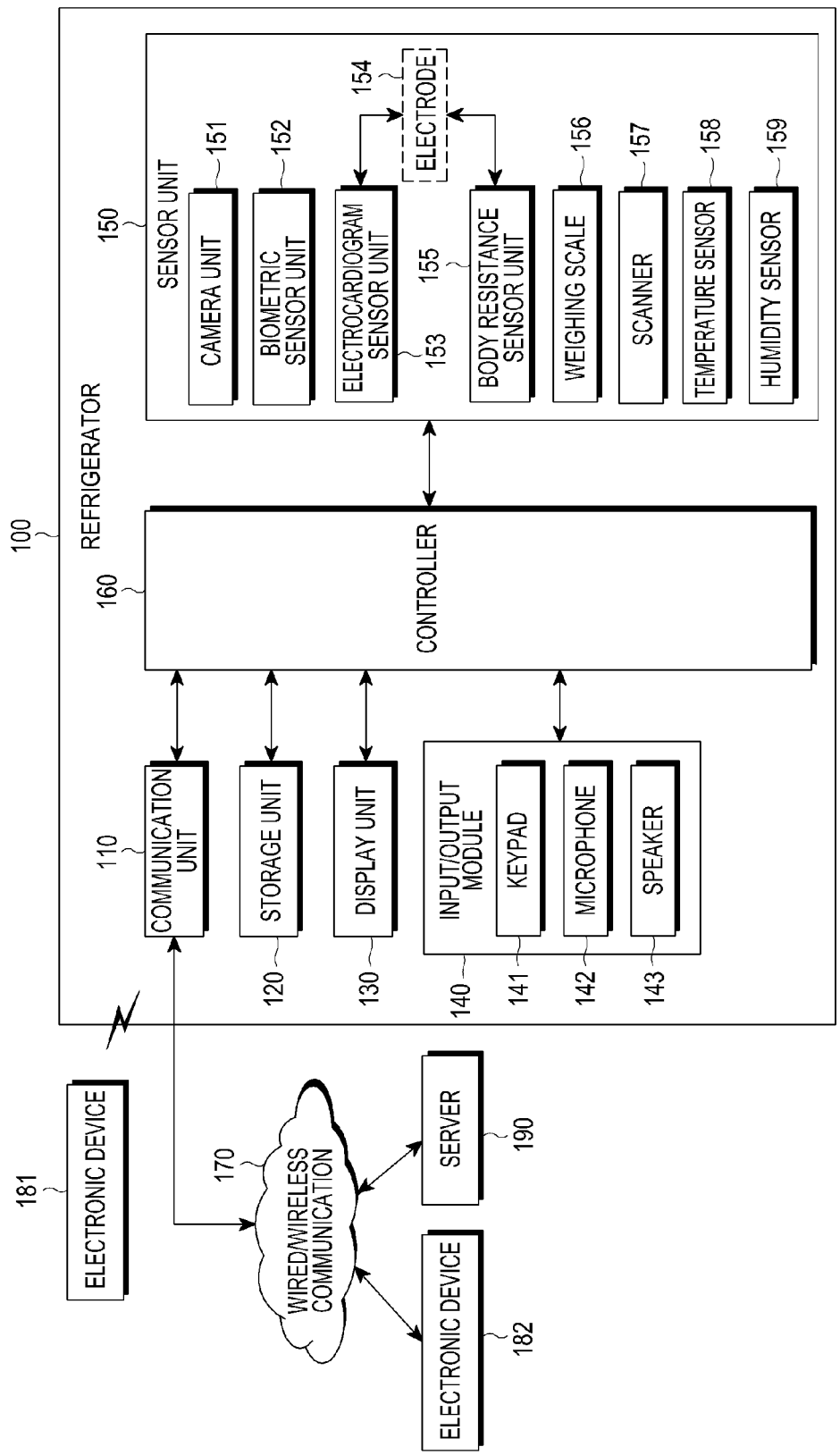
FIG. 1 illustrates a configuration of a refrigerator according to an exemplary embodiment.

Hereinafter, terms that are used in the specification will be briefly described, and exemplary embodiments will be described in detail. The drawings may not be to scale, and the relative size, proportions, and depiction of elements in the drawings may be exaggerated for clarity, illustration, and convenience.

The following detailed description is provided to assist the reader in gaining a comprehensive understanding of the methods, apparatuses, and/or systems described herein. However, various changes, modifications, and equivalents of the methods, apparatuses and/or systems described herein will be apparent to one of ordinary skill in the art. The progression of processing steps and/or operations described is an example; however, the sequence of and/or operations is not limited to that set forth herein and may be changed as is known in the art, with the exception of steps and/or operations necessarily occurring in a certain order. Also, descriptions of functions and constructions that are well known to one of ordinary skill in the art may be omitted for increased clarity and conciseness.

The features described herein may be embodied in different forms, and are not to be construed as being limited to the examples described herein. Rather, the examples described herein have been provided so that this disclosure will be thorough and complete, and will convey the full scope of the disclosure to one of ordinary skill in the art.

All terms including descriptive or technical terms used herein should be construed as having meanings that are obvious to one of ordinary skill in the art. However, the terms may have different meanings according to an intention of one of ordinary skill in the art, precedent cases, or the appearance of new technologies. Also, some terms may be arbitrarily selected by the applicant, and in this case, the meaning of the selected terms will be described in detail in the detailed description of the disclosure. Thus, the terms used herein have to be defined based on the meaning of the terms together with the description throughout the specification.

Also, when a part "includes" or "comprises" an element, unless there is a particular description contrary thereto, the part can further include other elements, not excluding the other elements. In the following description, terms such as "unit" and "module" indicate a unit for processing at least one function or operation, wherein the unit and the block may be embodied as hardware or software or embodied by combining hardware and software.

One or more exemplary embodiments of the present disclosure will now be described more fully with reference to the accompanying drawings. However, the one or more exemplary embodiments of the present disclosure may be embodied in many different forms, and should not be construed as being limited to the exemplary embodiments set forth herein. Rather, these exemplary embodiments are provided so that this disclosure will be thorough and complete, and will fully convey the concept of the one or more exemplary embodiments of the present disclosure to those of ordinary skill in the art. In the following description, well-known functions or constructions are not described in detail because the well-known functions would obscure the one or more exemplary embodiments of the present disclosure with unnecessary detail. Like reference numerals in the drawings denote like or similar elements throughout the specification.

A refrigerator may be an electronic device for storing food, such as, a general multi-purpose refrigerator including a fridge and a freezer, a kimchi refrigerator, a wine refrigerator, a deep-freezer, a cosmetic cooler, a portable refrigerator, a refrigerator for vehicles, a draft beer refrigerator, a rice refrigerator, a side dish refrigerator, or the like. The refrigerator may be a single door refrigerator, a two-door refrigerator, a four-door refrigerator, or the like.

The refrigerator may communicate with another electronic device, and the refrigerator may receive information associated with the life or health of a user from another electronic device. The communication may performed wirelessly or via a wired connection.

An electronic device may include a communication function. For example, the electronic device may be at least one of a smart phone, a tablet Personal Computer (PC), a mobile phone, a video phone, an e-book reader, a desktop PC, a laptop PC, a netbook computer, a Personal Digital Assistant (PDA), a Portable Multimedia Player (PMP), an MP3 player, a mobile medical device, a camera, a wearable device, a Head-Mounted-Device (HMD), electronic glasses, electronic clothes, an electronic bracelet, an electronic necklace, an electronic appcessory, an electronic tattoo, and a smart watch.

Further, an electronic device may be a smart home appliance with a communication function. The smart home appliance as an example of the electronic device may include at least one of, a television, a Digital Video Disk (DVD) player, an audio system, a refrigerator, an air conditioner, a vacuum cleaner, an oven, a microwave oven, a washing machine, an air cleaner, a set-top box, a TV box (e.g., Samsung HomeSync™, Apple TV™, or Google TV™), a game console, an electronic dictionary, an electronic key, a camcorder, and an electronic picture frame.

In addition, the electronic device may include at least one of various medical devices, for example, a weighing scale, a blood pressure gauge, a body fat measuring device, a Magnetic Resonance Angiography (MRA) scanner, a Magnetic Resonance Imagining (MRI) scanner, a Computed Tomography (CT) scanner, and an ultrasonic device.

Further, an electronic device may include at least one of a part of furniture or a building/structure having a communication function, an electronic board, an electronic signature receiving device, a projector, and various types of measuring instruments (for example, a water meter, an electric meter, a gas meter, a radio wave meter, and the like). The electronic device according to the present disclosure may be a combination of one or more of the aforementioned various devices. Further, it will be appreciated by those skilled in the art that the electronic device according to the present disclosure is not limited to the aforementioned devices.

FIG. 1 is a diagram illustrating a configuration of a refrigerator according to an aspect of an exemplary embodiment of the present disclosure.

A refrigerator 100 includes a communication unit 110, a storage unit 120, a display unit 130, an input/output module 140, a sensor unit 150, and a controller 160.

The communication unit 110 may be connected to a server 190 or an electronic device 181 and 182, directly or through a network, and may be a wired or wireless communication unit. The communication unit 110 may transmit data from the controller 160, the storage unit 120, the camera unit 151, or the like, or may receive data from an external communication line or the air, so as to transfer the same to the controller 160 or to store the same in the storage unit 120.

The communication unit 110 may include a mobile communication module, a wireless LAN module, a short-range communication module, or the like. The communication unit 110 may include a communication card, a communication interface, a communication modem, or the like. For example, the communication unit 110 may include an Integrated Services Digital Network (ISDN) card, a modem, a Local Area Network (LAN) card, an infrared port, a Bluetooth port, a Zigbee port, a wireless port, or the like. The communication unit 110 may support a wired/wireless communication 170, such as, predetermined short-range wired and wireless communication (for example, Wifi), Bluetooth (BT), Radio Frequency Identification (RFID), Near Field Communication (NFC), predetermined network communication (for example, Internet, Local Area Network (LAN), Wire Area Network (WAN), telecommunication network, cellular network, satellite network, Universal Serial Bus (USB), Recommended Standard 232 (RS-232), Plain Old Telephone Service (POTS), and the like.

The mobile communication module may connect the refrigerator 100 to the server 190 or the electronic device 182, through the mobile communication using one or more antennas, based on a control of the controller 160. The mobile communication module may exchange data for a voice call, a video call, a Short Message Service (SMS), a Multimedia Message Service (MMS), or the like with a portable phone, a smart phone, a computer or another device including a phone number or a network address that may be input into the refrigerator 100, or may transmit or receive a Radio Frequency (RF) signal for a uni-direction transmission or reception.

The wireless LAN module may be connected to the Internet according to a control of the control unit 160 according to an aspect of an exemplary embodiment wherein a wireless Access Point (AP) (not illustrated) is installed. The wireless LAN module may support the wireless LAN standard of the Institute of Electrical and Electronic Engineers (IEEE).

The short-range communication module may support a wireless short-range communication between the refrigerator 100 and the electronic device 181, based on a control of the controller 160.

The storage unit 120 may store data for operating one or more applications. The storage unit 120 may store images to provide a Graphical User Interface (GUI) related to one or more applications, databases or data (user information, documents and the like), background images (a menu screen, an idle screen, and the like), operating programs for operating the refrigerator 100, images captured by a camera, and the like. The memory 120 may be a medium which is readable using a machine (for example, computer) and the term, "machine-readable medium," may be defined as a medium that provides data for the machine so that the machine may perform a specific function. The machine-readable medium may be a storage medium. The storage unit 120 may include a non-volatile medium, a volatile medium, or the like. All of these media should be tangible so that commands transferred by the media are detected by a physical instrument through which the machine reads the commands.

The storage unit 120 may include an embedded memory or an external memory. The embedded memory may include, for example, at least one of a volatile memory (for example, a Dynamic Random Access Memory (DRAM), a Static RAM (SRAM), a Synchronous Dynamic RAM (SDRAM), or the like), and a non-volatile memory (for example, One Time Programmable Read Only Memory (OTPROM), a Programmable ROM (PROM), an Erasable and Programmable ROM (EPROM), an Electrically Erasable and Programmable ROM (EEPROM), a mask ROM, a flash ROM, a NAND flash memory, a NOR flash memory, or the like). The embedded memory may be a Solid State Drive (SSD). The external memory may include a flash drive, for example, a Compact Flash (CF), a Secure Digital (SD), a Micro Secure Digital (Micro-SD), a Mini Secure Digital (Mini-SD), an eXtreme Digital (xD), a memory stick, or the like. The refrigerator 100 may further include a storage device (or a storage medium) such as a hard drive device.

The display unit 130 may provide a Graphical User Interface (GUI) corresponding to various services (for example, a call, data transmission, broadcasting and still image/moving image photographing) to the user. The display unit 130 may detect one or more inputs input into a graphic user interface, and transmit user input information which is a result of the detection, to the controller 160. The display unit 130 may receive an input of one or more touches through a body part (for example, a finger) of a user or a touch input means (for example, a stylus pen). In addition, the display unit 130 may receive an input of a continuous motion of a single touch (for example, dragging). The display unit 130 may transmit user input information corresponding to the continuous motion of the input touch to the controller 160.

A user input may not be limited to a contact between the display unit 130 and a body part of the user or a touchable input means, and may include a hover (for example, a detectable interval between the display unit 130 and the body part of the user or the touchable input means is greater than 0 and less than or equal to 5 cm). The detectable interval may increase based on a capability of detecting a hovering by the display unit 130.

The display unit 130 may be a touch screen including a display panel and a touch panel. The touch screen may be, for example, a resistive touch screen, a capacitive touch screen, an infrared touch screen, an acoustic wave touch screen, an ElectroMagnetic (EM) touch screen, an Electro-Magnetic Resonance (EMR) touch screen, or the like. The display panel may be, for example, a Liquid Crystal Display (LCD), an Active Matrix Organic Light Emitting Diode (AM-OLED), or the like.

The input/output module 140 may be a means for receiving a user input or for informing a user of information, and may include a button, a keypad 141, a microphone 142, a speaker 143, a connector, cursor direction keys, a cursor control, or a partial or whole combination thereof.

The button may be formed on the front side of the refrigerator 100, and may include a power/lock button, a volume button, a menu button, a home button, a back button, a search button, or a partial or whole combination thereof.

The keypad 141 may receive a key input from a user to control the refrigerator 100. The keypad 141 may include a physical keypad formed in the refrigerator 100, a virtual keypad displayed on the display unit 130, or the like.

The microphone 142 may receive a voice or a sound to generate an electrical signal.

The speaker 143 may output various sounds corresponding to various signals (for example, a wireless signal, a digital audio file, a digital video file, a photographing signal, or the like), based on a control of the controller 160. The speaker 143 may output a sound corresponding to a function performed by the refrigerator 100. One or more speakers 143 may be formed at various locations on the refrigerator 100.

A connector may be used as an interface for connecting the refrigerator 100 and an electronic device. Through a wired cable connected to the connector based on a control of the controller 160, data stored in the storage unit 120 of the refrigerator 100 may be transmitted to the electronic device, or data may be received from the electronic device.

The sensor unit 150 may include one or more (i.e., a partial or whole combination) of a camera unit 151, a biometric sensor unit 152, an electrocardiogram sensor unit 153, a body resistance sensor unit 155, a weighing scale 156, a scanner 157, a temperature sensor unit 158, and a humidity sensor unit 159.

The camera unit 151 may include at least one camera, and each camera may include a lens system that executes convergence of light incident from the outside so as to form an optical image of a subject, and an image sensor configured to convert an optical image into an electric image signal or data so as to output the same, and may further include a flash and the like.

In addition, at least one camera may include an infrared camera, and the infrared camera may include an infrared light source that is configured to output infrared light, and an image sensor that is configured to detect infrared light reflected from a subject, convert the detected infrared light into an electric image signal or data, and output the same.

The camera unit 151 may be configured to photograph the upper body and/or the lower body of a user, and output the photographed body image to the controller 160.

The biometric sensor unit 152 may include a fingerprint sensor, an iris sensor, or the like. The biometric sensor unit 152 may be configured to output recognized user biometric information to the controller 160.

The electrocardiogram sensor unit 153 may be configured to measure an electrocardiogram of the user using an electrode unit 154. The electrode unit 154 may include first through fourth electrodes. The first and second electrodes, for example, may make contact with the left hand among the body parts of a user, and the third and fourth electrodes may make contact with the right hand among the body parts of the user. The electrocardiogram sensor unit 153 may measure an electrocardiogram using only the first and third electrodes, or using only the second and fourth electrodes, or may further use another electrode (for example, the second or the first electrode) to enable the user to be grounded. For example, the electrocardiogram sensor unit 153 may measure a voltage between the first and the third electrodes, and a voltage waveform that varies over time indicates an electrocardiogram signal. The electrocardiogram sensor unit 153 may output measured electrocardiogram information (that is, an electrocardiogram signal), to the controller 160.

The body resistance sensor unit 155 may be configured to measure a body resistance of a user, using the electrode unit 154. For example, the first and second electrodes may be in contact with the left hand of a user and the third and fourth electrodes may be in contact with the right hand of the user. The body resistance sensor unit 155 may apply a current of a predetermined intensity to the user through the first and fourth electrodes, measure a voltage value between the second and the third electrodes, and calculate a resistance value using a relationship (V=IR) among a voltage (V), a current (I), and a resistance (R). The body resistance sensor unit 155 may output the measured body resistance information (a voltage value or a calculated body resistance value), to the controller 160.

The weighing scale 156 may be configured to measure a weight of a user, and output the measured weight value to the controller 160. The weighing scale 156 may include a second electrocardiogram sensor unit and/or a second body resistance sensor unit, and may output electrocardiogram information and/or body resistance information of the user to the controller 160.

The scanner 157 may recognize food identification information that is attached to food to be stored in the refrigerator 100, and output the recognized food identification information to the controller 160. For example, the food identification information may be a barcode, a Quick Response (QR) code, a Near Field Communication (NFC) tag, a Radio Frequency Identification (RFID), or the like.

The temperature sensor unit 158 may be configured to measure the temperature inside and/or outside the refrigerator 100, and may output the measured temperature value to the controller 160.

The humidity sensor unit 159 may measure the humidity inside and/or outside the refrigerator 100, and may output the measured humidity value to the controller 160.

The controller 160 may be configured to execute a program operation set in advance, or a program operation based on user input information. In this instance, a user input may include an input provided through the input/output module 140, the display unit 130, the sensor unit 150, the communication unit 110, or the like. The controller 160 may include a bus for information communication, and a processor connected with the bus for information processing. The controller 160 may include a Central Processing Unit (CPU), an Application Processor (AP), or the like.

The controller 160 may further include a Random Access Memory (RAM) connected to the bus for temporarily storing information required by the processor, a Read Only Memory (ROM) connected to the bus for storing static information required by the processor, and the like.

The controller 160 may be configured to control general operations of the refrigerator 100, and may provide a health service providing method according to various embodiments of the present disclosure.

Figure 2:
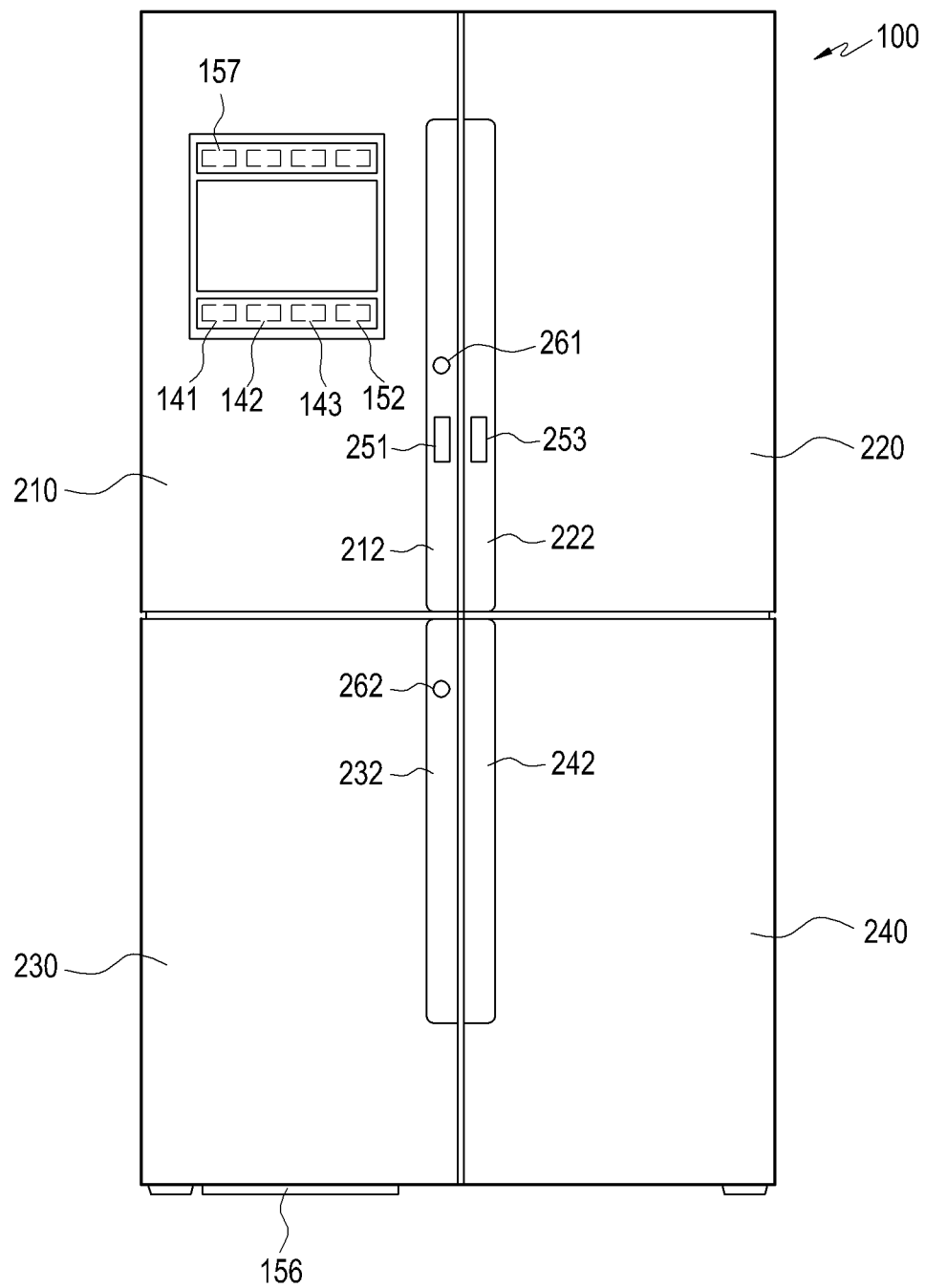
FIG. 2 illustrates a front side of a refrigerator according to an exemplary embodiment.
Figure 3:
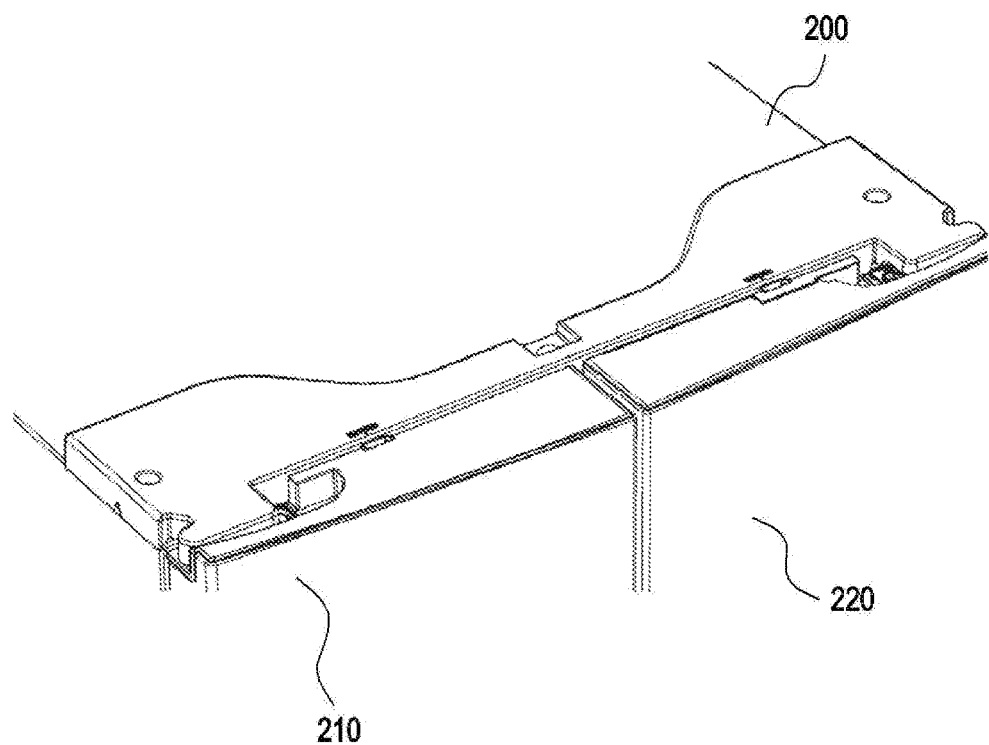
FIG. 3 is a top view of a refrigerator according to an exemplary embodiment.

FIG. 2 illustrates the front side of the refrigerator 100 according to an aspect of an embodiment of the present disclosure, and FIG. 3 is a top view of the refrigerator 100.

The refrigerator 100 may include a main body 200, and at least one door. The refrigerator 100 may include first through fourth doors 210, 220, 230, and 240, and the first through fourth doors 210, 220, 230, and 240 may include first through fourth handles 212, 222, 232, and 242, respectively.

The display unit 130, elements of the input/output module 140, the biometric sensor unit 152, and the scanner 157 may be disposed in the front side of the first door 210. The elements of the input/output module 140 located in the front side of the first door 210 may include the keypad 141, the microphone 142, and the speaker 143.

A first electrode 251 may be disposed in the front side of the first handle 212 of the first door 210, and a second electrode 252 may be disposed in the back side of the first handle 212. A third electrode 253 may be disposed in the front side of the second handle 220 of the second door 222, and a fourth electrode 254 may be disposed in the back side of the second handle 222.

In the front side of the first handle 212 of the first door 210, a first camera 261 may be disposed in the upper side of the first electrode 251. A second camera 262 may be disposed in the front side of the third handle 232 of the third door 230. The first camera 261 may be configured to photograph the upper body of a user, and the second camera 262 may be configured to photograph the lower body of the user.

Figure 4:
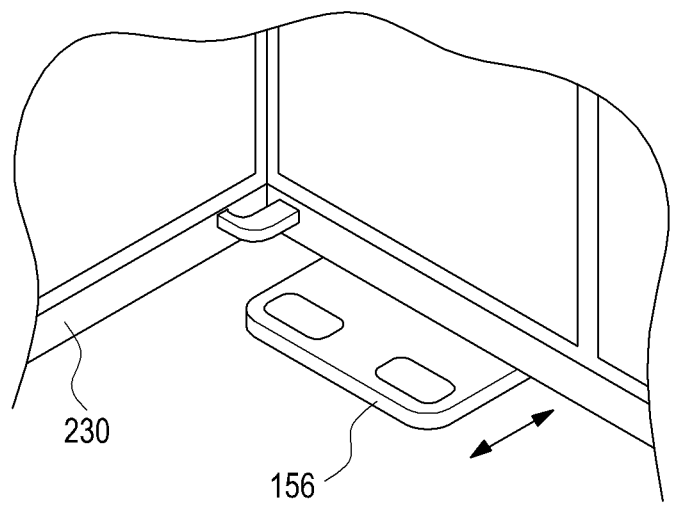
FIG. 4 illustrates a weighing scale installed in a refrigerator according to an exemplary embodiment.
Figure 5:
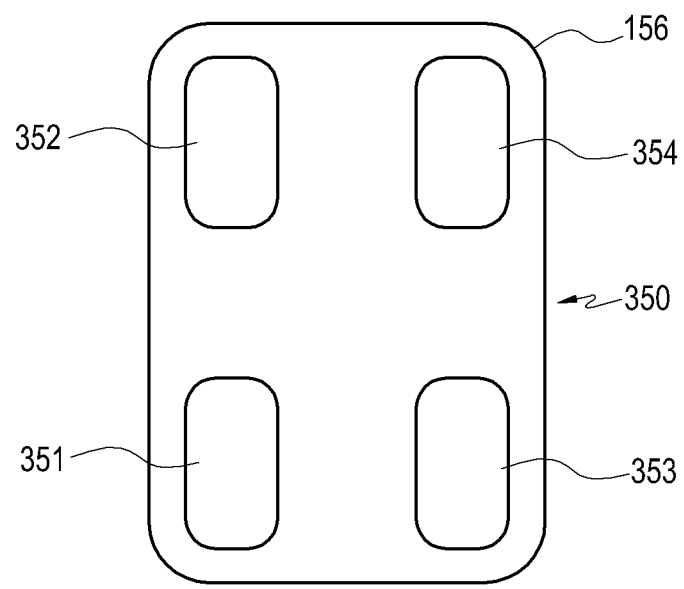
FIG. 5 is a plan view of a weighing scale according to an exemplary embodiment.

FIG. 4 illustrates the weighing scale 156 installed in the refrigerator 100 according to an aspect of an exemplary embodiment, and FIG. 5 is a plan view of the weighing scale 156, which is separated from the refrigerator 100 according to an aspect of an exemplary embodiment.

The main body 200 of the refrigerator 100 may be in a shape of a box of which the front side is open, and may include a left side part, a right side part, a top side part, a bottom side part, a back side part, and a middle part disposed between first and second doors and the third and fourth doors. The weighing scale 156 may be drawn in or out in a sliding manner, from the bottom side part of the main body 200 or under the same.

The weighing scale 156 may include a second electrode unit 350, the second electrode unit 350 may include first through fourth electrodes 351, 352, 353, and 354, and the first and second electrodes 351 and 352 may make contact with the left foot of a user and the third and fourth electrodes 353 and 354 may make contact with the right foot of the user. The weighing scale 156 may include a second electrocardiogram sensor unit (not illustrated) and/or second body resistance sensor unit (not illustrated). The second electrocardiogram sensor unit may measure an electrocardiogram using only the first and third electrodes 351 and 353, or using only the second and fourth electrodes 352 and 354, or may additionally use another electrode (for example, the second electrode 352 or the first electrode 351). The second body resistance sensor unit may be configured to apply a current of a predetermined intensity to a user through the first through fourth electrodes 351 through 354, measure a voltage value between the second electrode 352 and third electrode 353, and output measured body resistance information (a voltage value or a calculated body resistance value) to the controller 160. In addition, the weighing scale 156 may be configured to measure the weight of a user, and output the measured weight value to the controller 160.

Figure 6:
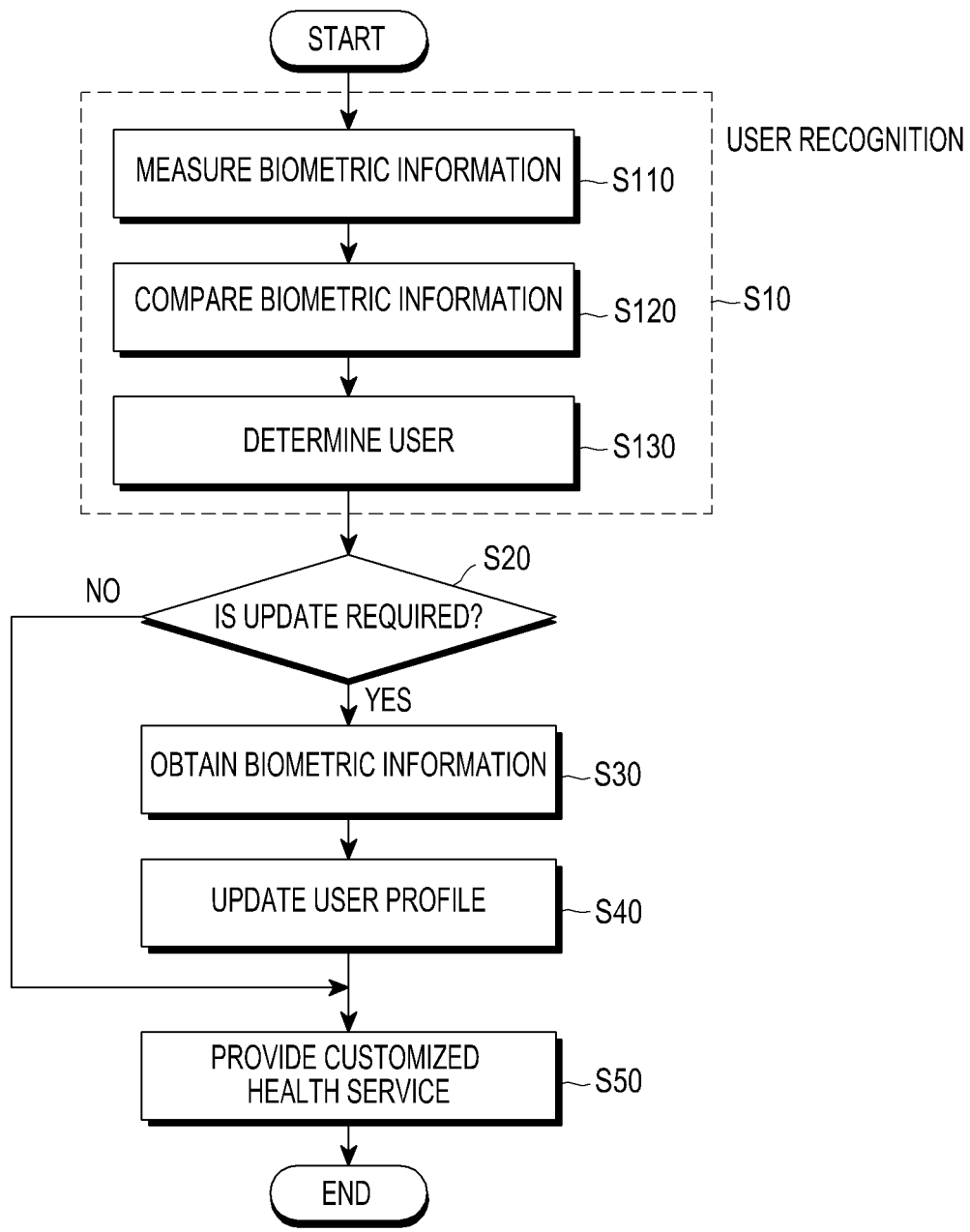
FIG. 6 is a flowchart illustrating a health service providing method according to an exemplary embodiment.

FIG. 6 is a flowchart illustrating a health service providing method according to an aspect of an exemplary embodiment of the present disclosure.

Operation S10 corresponds to a user recognition operation that includes measuring biometric information in operation S110, comparing the measured biometric information with biometric information stored in the storage unit 120 in operation S120, and determining a user based on a result of comparison in operation S130.

The controller 160 may recognize a user through the display unit 130, the input/output module 140 or the sensor unit 150.

As an example of the user recognition, the controller 160 provides a user authentication screen in the display unit 130, a user inputs secret information required by the user authentication screen through the display unit 130 or the input/output module 140, and the controller 160 compares the secret information input by the user with secret information registered on a user profile stored in the storage unit. The controller 160 may determine that a user of the user profile is recognized when the secret information input by the user is identical to the secret information of the user profile. According to various aspects of exemplary embodiments, the input of the secret information may include one or more of an input provided through a virtual or physical keypad, a voice input, a gesture input provided through a camera, a biometric information input such as an iris, a fingerprint, or the like, provided through the biometric sensor unit 152, or the like. The controller 160 may provide a user authentication screen in response to the various inputs.

Figure 7:
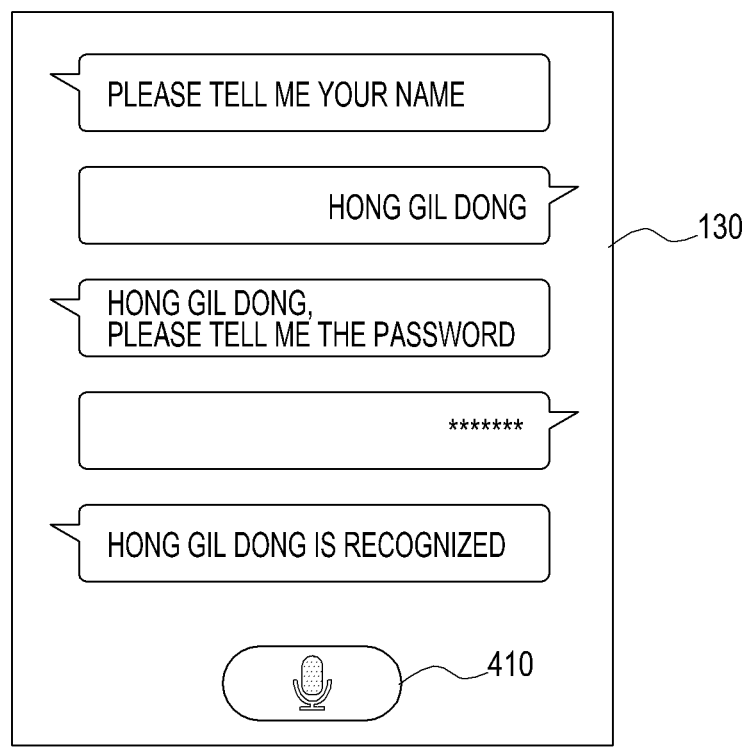
FIG. 7 illustrates user recognition through voice recognition according to an exemplary embodiment.

FIG. 7 illustrates an example of user recognition through voice recognition according to an aspect of an exemplary embodiment of the present disclosure.

The controller 160 displays a sign reading "Please tell me your name." on the display unit 130. A voice recognition button is provided on the lower end of the display unit 130, and a user selects a voice recognition button 410 so as to execute a voice recognition mode. Alternatively, the voice recognition mode may be automatically executed by the controller 160.

When the user answers, "Hong Gil Dong", the controller 160 recognizes the voice of the user, input through the microphone 142, and displays the recognized content on the display unit 130. In addition, the controller 160 may search for a user profile having a name of "Hong Gil Dong" from a user profile database stored in the storage unit 120.

Subsequently, the controller 160 displays, on the display unit 130, a sign reading "Hong Gil Dong, please tell me the password." When the user answers with the password, the controller 160 compares the password of the retrieved user profile with the password input by the user, and displays a result of the comparison on the display unit 130. For example, when the comparison is successful, the controller 160 displays the phrase reading "Hong Gil Dong is recognized", on the display unit 130. When the comparison fails, the controller 160 displays, on the display unit 130, a phrase reading "Please tell me the password, again" or "Hong Gil Dong is not recognized."

According to an aspect of an exemplary embodiment, the controller 160 may transmit a voice of the user (and user name information) to the server 190, and may execute an operation based on a voice recognition result received from the server 190.

According to an aspect of an exemplary embodiment, when the user says, "Hong Gil Dong", the controller 160 recognizes a voice of the user input through the microphone 142, searches for a user profile having a name of Hong Gil Dong from the user profile database stored in the storage unit 120, compares voice print information of the retrieved user profile with voice print information of the input voice of the user, and displays a sign reading "Hong Gil Dong is recognized" on the display unit 130 when the comparison is successful.

Figure 8:
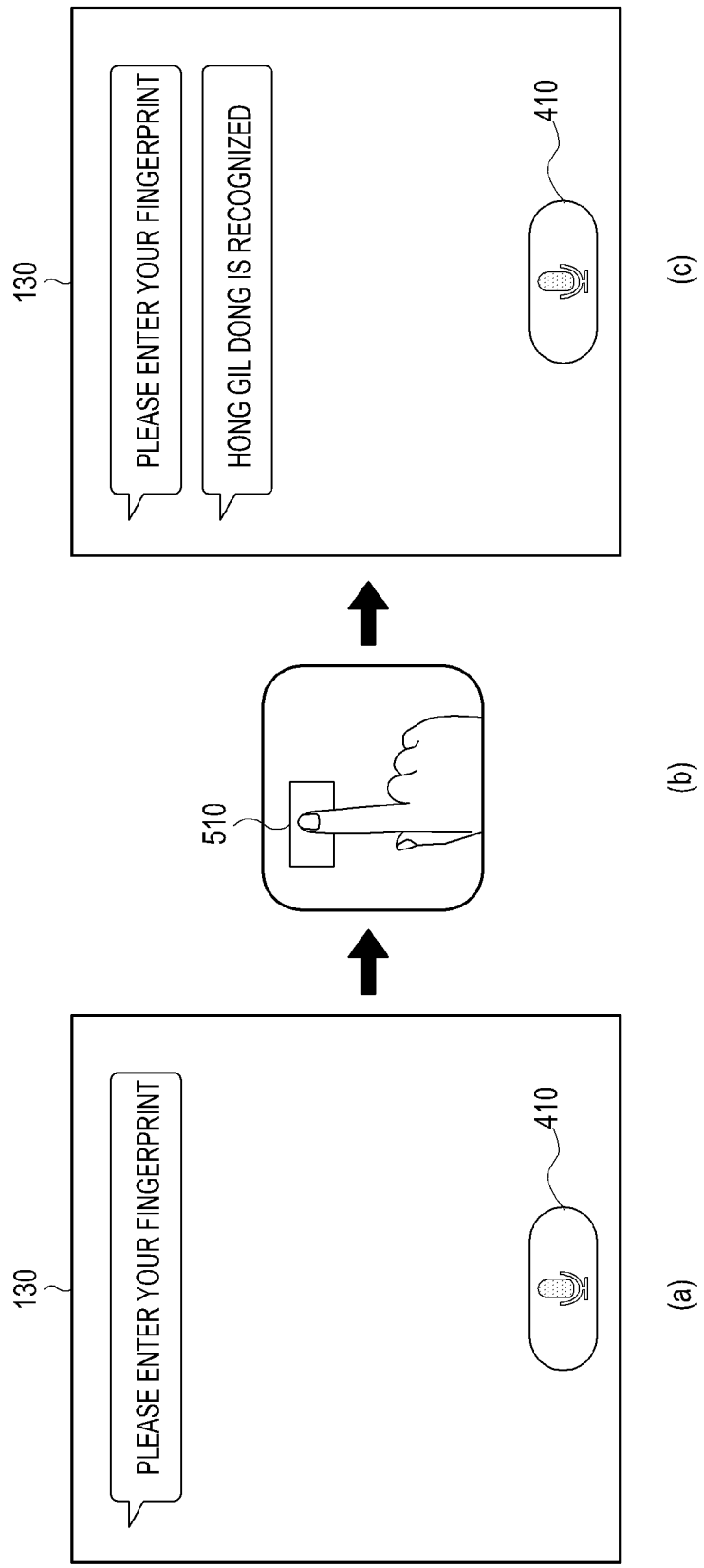
FIG. 8 illustrates user recognition through fingerprint recognition according to an exemplary embodiment.

FIG. 8 illustrates an example of user recognition through fingerprint recognition according to an aspect of an exemplary embodiment of the present disclosure.

Referring to (a) of FIG. 8, the controller 160 may control the display unit 130 to display a sign reading "Please tell me your name." A voice recognition button 410 may be provided on the lower end of the display unit 130, and a user may select a voice recognition button so as to execute a voice recognition mode. Alternatively, the voice recognition mode may be automatically executed by the controller 160.

Referring to (b) of FIG. 8, the biometric sensor unit 152 may include a fingerprint sensor 510. The fingerprint sensor 510 generates fingerprint data corresponding to a fingerprint pattern of a finger in contact with a surface of the fingerprint sensor 510. The fingerprint sensor 510 outputs the generated fingerprint data to the controller 160. The controller 160 may recognize fingerprint pattern information of the user from the fingerprint data received from the fingerprint sensor 510.

The controller 160 searches the storage unit 120 for a user profile having fingerprint pattern information identical to the input fingerprint pattern, and displays a search result on the display unit 130.

Referring to (c) of FIG. 8, when a user is successfully recognized, the controller 160 displays, on the display unit 130, a sign identifying the recognized user. For example, the display unit 130 may read, "Hong Gil Dong is recognized", thereby referencing a user name of the retrieved user profile.

Figure 9:
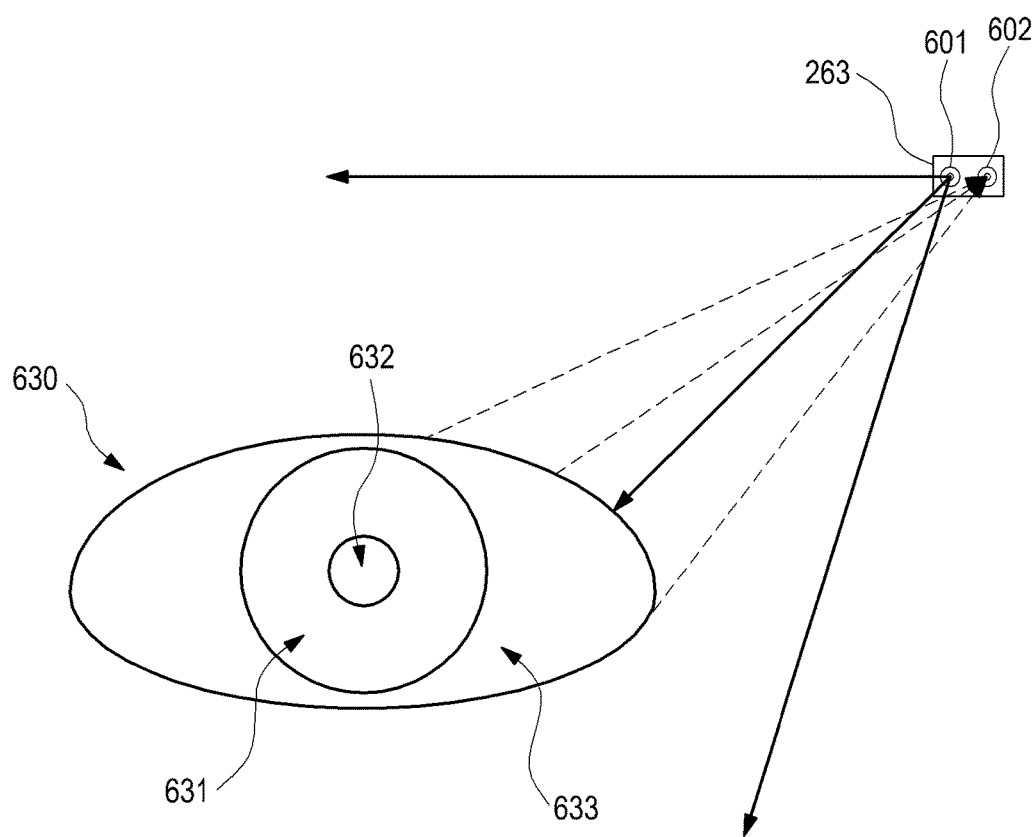
FIG. 9 illustrates user recognition through iris recognition according to an exemplary embodiment.

FIG. 9 illustrates an example of user recognition through iris recognition according to an aspect of an exemplary embodiment of the present disclosure.

Referring to FIG. 9, the controller 160 controls an infrared light source 601 of the third camera 263 to output an infrared light modulated to a low frequency or an infrared light having a uniform intensity.

An image sensor 602 of the third camera 263 converts an optical image formed by an infrared light reflected from a subject, into an electric image, and outputs the electric image. The controller 160 may recognize an iris from the electric image.

According to an aspect of an exemplary embodiment, the controller 160 may measure biometric information on an eye, a fingerprint, a face, a hand, a wrist, a blood vessel (such as a vein), or the like, through the third camera 263.

An eye 630 generally has a pupil 631, an iris 632, and a sclera 633. The infrared light source 601 may emit infrared light to the eye 630 of the user, and the image sensor 602 may photograph the eye 630 of the user and output an eye image. The controller 160 may be configured to compare iris data (an iris image, feature point information, or the like) of the user data stored in the storage unit 120 with the photographed eye image, so as to recognize the iris of the user. The iris data of the user may be included in a user profile.

According to an aspect of an exemplary embodiment, the controller 160 may recognize a user based on a gesture or a motion of the user. When the user is relatively close to the refrigerator 100 or the user touches the refrigerator 100, the controller 160 may provide a user authentication screen on the display unit. Alternatively, the controller 160 may execute the user recognition when a gaze of the user stays on the refrigerator 100 during a predetermined period of time, when the user draws out the weighing scale 156, and the like.

Figure 10A:
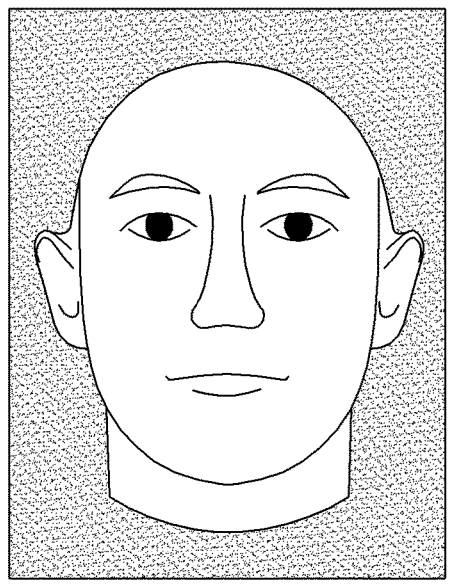
FIGS. 10A and 10B illustrate user recognition through facial recognition according to an exemplary embodiment.
Figure 10B:
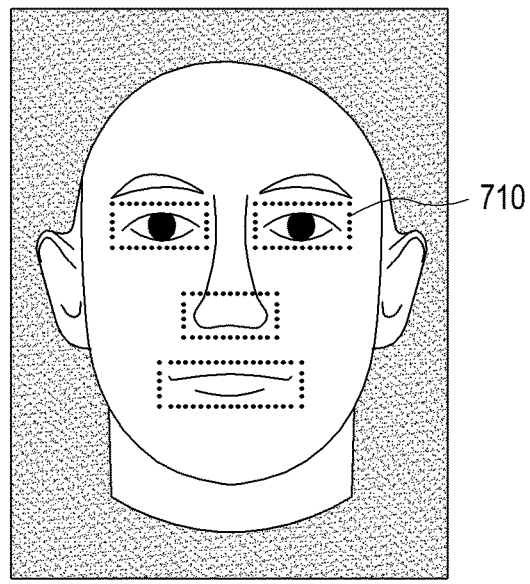

FIGS. 10A and 10B illustrate an example of user recognition through facial recognition according to an aspect of an exemplary embodiment of the present disclosure.

Referring to FIG. 10A, the controller 160 may determine whether a face is included in an image photographed by the first camera 261, and thereafter extract the corresponding facial features. Here, facial detection may be executed through a general facial detection method, and a facial extraction technology based on facial features such as the contour of a face, the color and/or texture of the facial skin, and/or the like may be used. For example, the controller 160 may learn faces through a plurality of facial images, and detect a face from an input image using the accumulated learned facial data.

Referring to FIG. 10B, the controller 160 may compare feature points 710 of a detected face with feature points of each user profile stored in the storage unit 120, search for a user profile that corresponds to the detected feature points, and determine that a user of the retrieved user profile is recognized.

That is, the controller 160 may search stored user profiles for a face that matches a face detected from the input image by comparing feature points, and thereby determining that a user of a user profile corresponding to the matched face is recognized.

Figure 11:
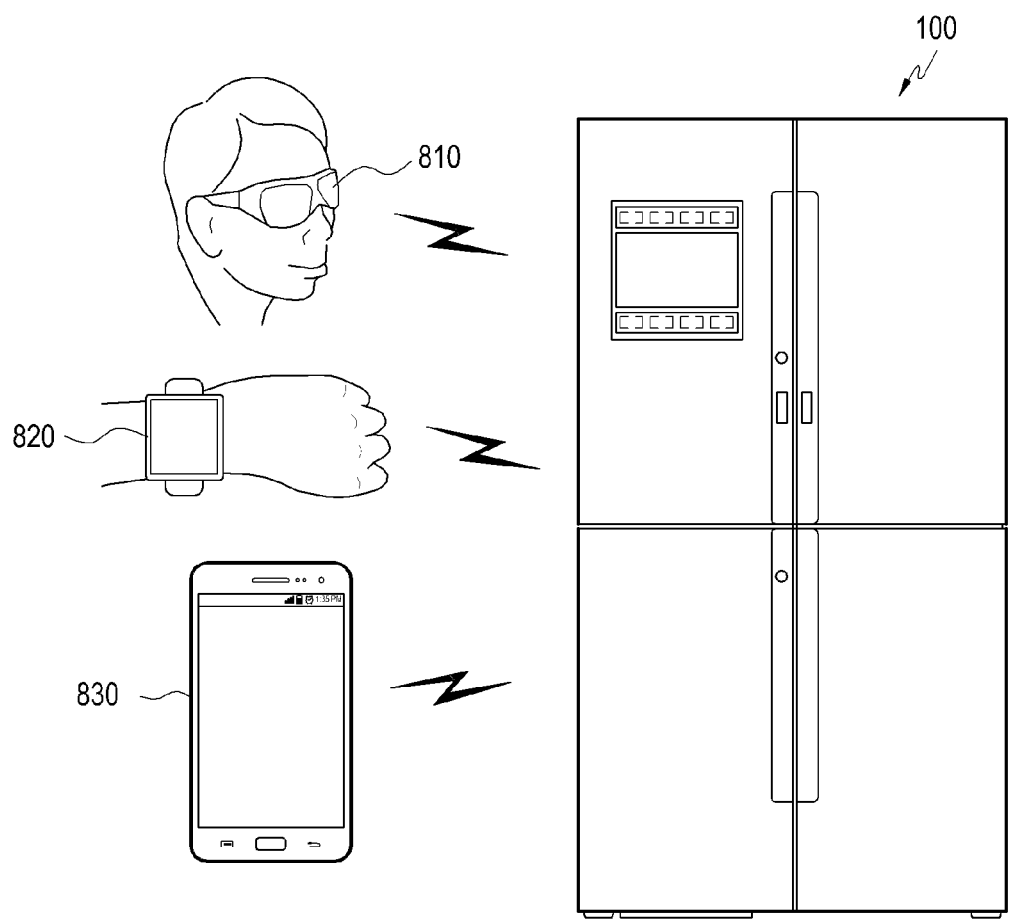
FIG. 11 illustrates user recognition through device recognition according to an exemplary embodiment.

FIG. 11 illustrates an example of user recognition through device recognition according to an aspect of an exemplary embodiment of the present disclosure.

The controller 160 may be configured to provide a Peer to Peer (P2P) service by executing short-range communication with a neighboring electronic device through the communication unit 110. The refrigerator 100 may communicate with a wearable electronic device, such as smart glasses 810, a smart watch 820, or the like, or a portable phone 830 including a short-range communication module. Exemplary short-range communication methods may correspond to Near Field Communication (NFC), Radio Frequency Identification (RFID), Bluetooth, Bluetooth Low Energy (BLE), Zigbee, Infrared communication, Wi-Fi Direct, home Radio Frequency (RF), Digital Living Network Alliance (DLNA), and the like. As part of the short-range communication, the controller 160 may search for a neighboring electronic device that supports short-range communication through the communication unit 110, and receive device information from the electronic device. The device information may include a model name of an electronic device determined by a manufacturer, such as SHV-E21OS, Android-99, or the like, or may include a name arbitrarily set by a corresponding user. The controller 160 may then search the storage unit 120 for a user profile having device information identical to the received device information, and thereafter determine that a user of the retrieved user profile is recognized.

Figure 12:
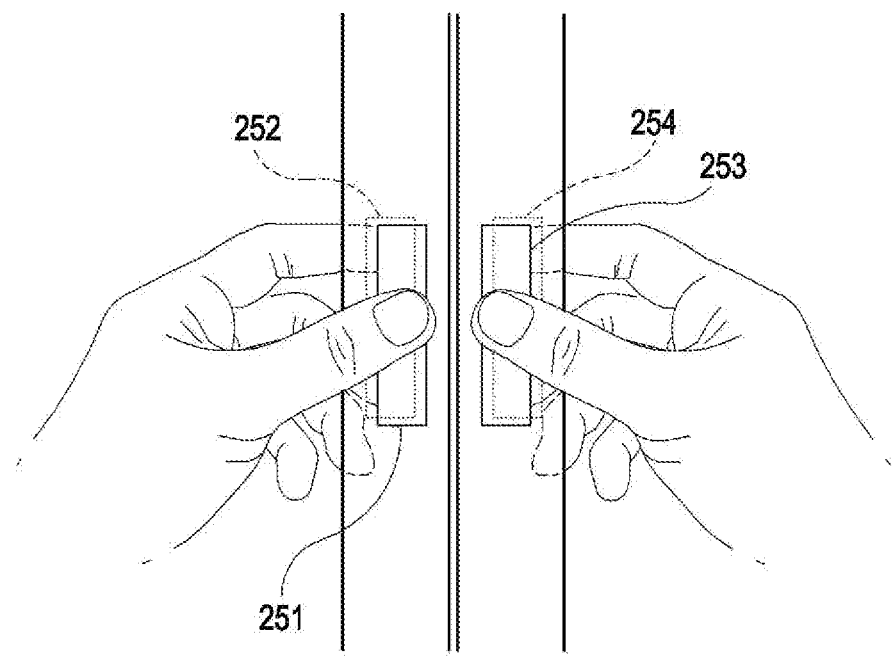
FIG. 12 illustrates user recognition through measuring an electrocardiogram according to an exemplary embodiment.

FIG. 12 illustrates an example of user recognition through measuring an electrocardiogram or recognition according to an aspect of an exemplary embodiment of the present disclosure.

The controller 160 may be configured to measure an electrocardiogram by controlling an electrocardiogram sensor unit 153. The electrocardiogram measurement may be performed, for example, when a user draws out the weighing scale 156 from the main body of the refrigerator 100 or holds a door of the refrigerator 100.

According to an aspect of an exemplary embodiment, a user may interact with the device such that the thumb of the left hand is in contact with the first electrode 251 and the index finger of the left hand is in contact with the second electrode 252, the thumb of the right hand is in contact with the third electrode 253, and the index finger of the right hand is in contact with the fourth electrode 254.

The electrocardiogram sensor unit 153 may use the second electrode 252 to ground the user, and measure a voltage between the first electrode 251 and the third electrode 253. In particular, the electrocardiogram sensor unit 153 may apply a common component voltage of the first and third electrodes 251 and 253 to the second electrode 252, to enable the user to be grounded, and amplify and output a voltage between the first electrode 251 and the third electrode 253. A voltage waveform that varies over time, which is output from the electrocardiogram sensor unit 153, indicates an electrocardiogram signal. The electrocardiogram signal represents a change over time in an action potential of a cardiac muscle cell, which occurs based on heart beats. In addition, the electrocardiogram sensor unit 153 may include an analog/digital converter configured to convert an analog electrocardiogram signal output through the first electrode 251 and the third electrode 253 into a digital electrocardiogram signal, and output the same to the controller 160.

The controller 160 searches the storage unit 120 for a user profile having an electrocardiogram signal or electrocardiogram identification information corresponding to the measured electrocardiogram signal or the identification information of the measured electrocardiogram signal, and determines that a user of the retrieved user profile is recognized.

Figure 13:
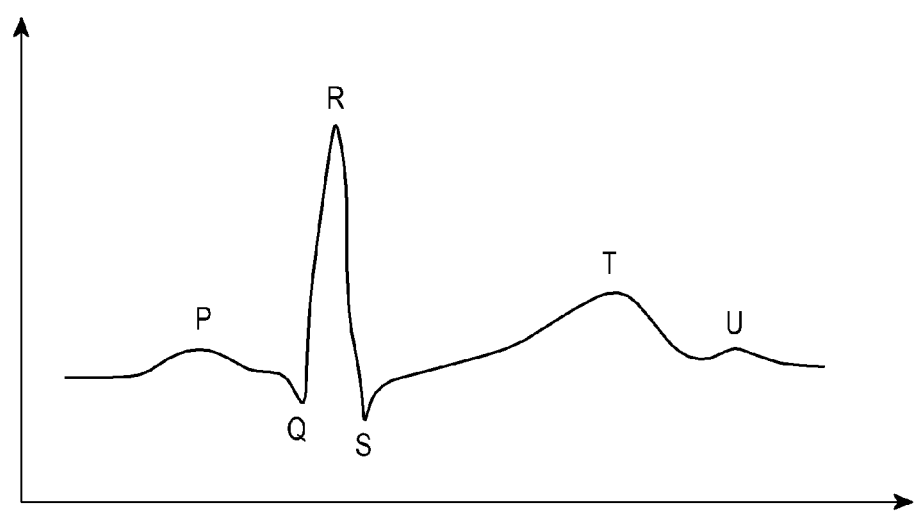
FIG. 13 illustrates an electrocardiogram signal.

FIG. 13 illustrates an electrocardiogram signal. In the electrocardiogram signal, the horizontal axis indicates time and the vertical axis indicate voltage. The electrocardiogram signal may be characterized by Q, R, S, T and U points.

Figure 14:
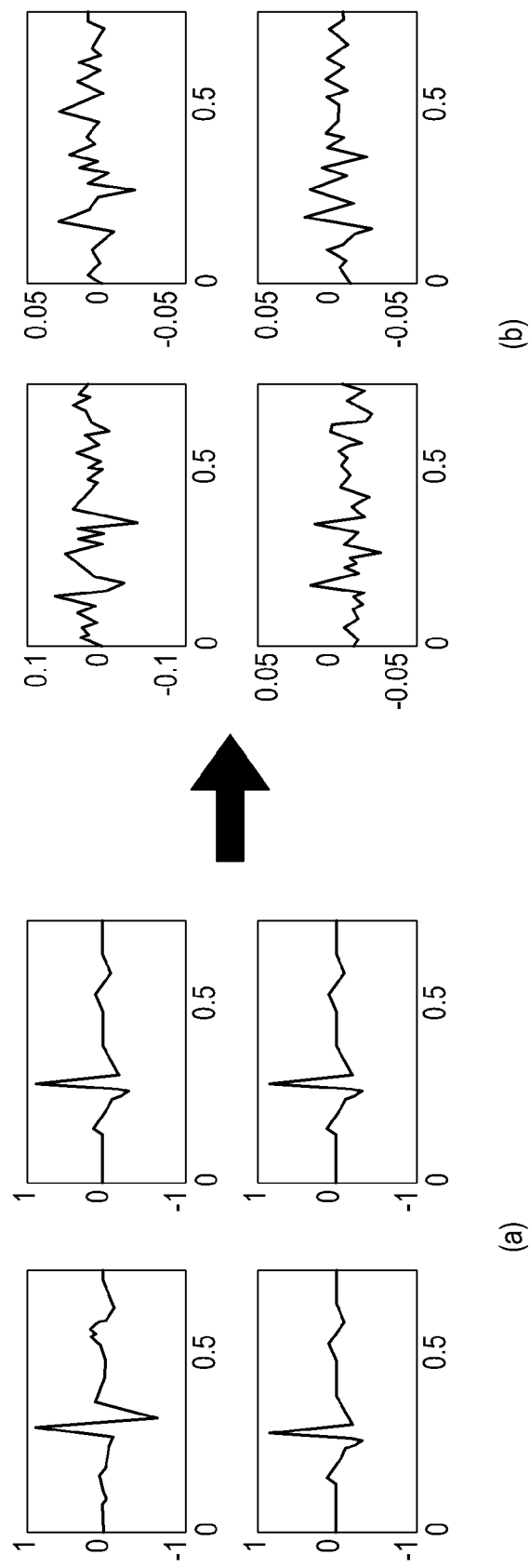
FIG. 14 illustrates an electrocardiogram signal.

FIG. 14 illustrates exemplary electrocardiogram signals, and that electrocardiogram identification information may be extracted from an electrocardiogram signal.

Electrocardiogram signals of four people are illustrated in (a) of FIG. 14, and (b) of FIG. 14 illustrates electrocardiogram identification information of the four people remaining after excluding a common component from the electrocardiogram signals of the four persons. Each electrocardiogram identification information is almost identical irrespective of a time and a date when the measurement is executed. Thus, the electrocardiogram identification information may be used as user recognition information.

FIG. 15 illustrates an example of user profiles according to an aspect of an exemplary embodiment of the present disclosure.

The user profile may include one or more of user identifiers 1, 2, and 3; user names A1, A2, and A3; electrocardiogram information B1, B2, and B3; body fat information C1, C2, and C3; body composition information D1, D2, and D3; muscle mass information E1, E2, and E3; pacemaker information indicating use of a pacemaker F1, F2, and F3; iris information G1, G2, and G3; fingerprint information H1, H2, and H3; voiceprint information I1, I2, and I3; age information J1, J2, and J3; sex information K1, K2, and K3; height information L1, L2, and L3; weight information M1, M2, and M3; skin color information N1, N2, and N3; eating habits information O1, O2, and O3; or a partial or whole combination thereof.

The eating habits information may include one or more of a pattern (time, duration, frequency, or the like) in which the user uses the refrigerator 100, a pattern (time, duration, frequency, or the like) in which the user intakes instant food such as frozen food or the like, a pattern in which the user intakes caffeine-containing food or beverages, high caloric food or beverages, or the like.

The controller 160 may execute user recognition by combining a plurality of pieces of biometric information of a user profile. For example, the controller 160 may accurately distinguish a user by combining electrocardiogram information and body fat information, and may compositively use another piece of biometric information (a fingerprint, a voice pint, a palm print (that is, a palmar crease), an iris, or the like), so as to increase the accuracy of distinguishing a user and expand the range of users.

Referring again to FIG. 6, operation S20 corresponds to an operation of determining whether to update a user profile. The controller 160 may set an update period for each identifier forming a user profile, and determine when each identifier needs to be updated.

Operation S30 corresponds to an operation of obtaining corresponding biometric information when the user profile needs to be updated. The controller 160 may obtain required biometric information, using the sensor unit 150 of the refrigerator 100, or from an adjacent electronic device.

Operation S40 corresponds to an operation of updating the user profile. The controller 160 may update the user profile of the corresponding user using the obtained biometric information.

Figure 16:
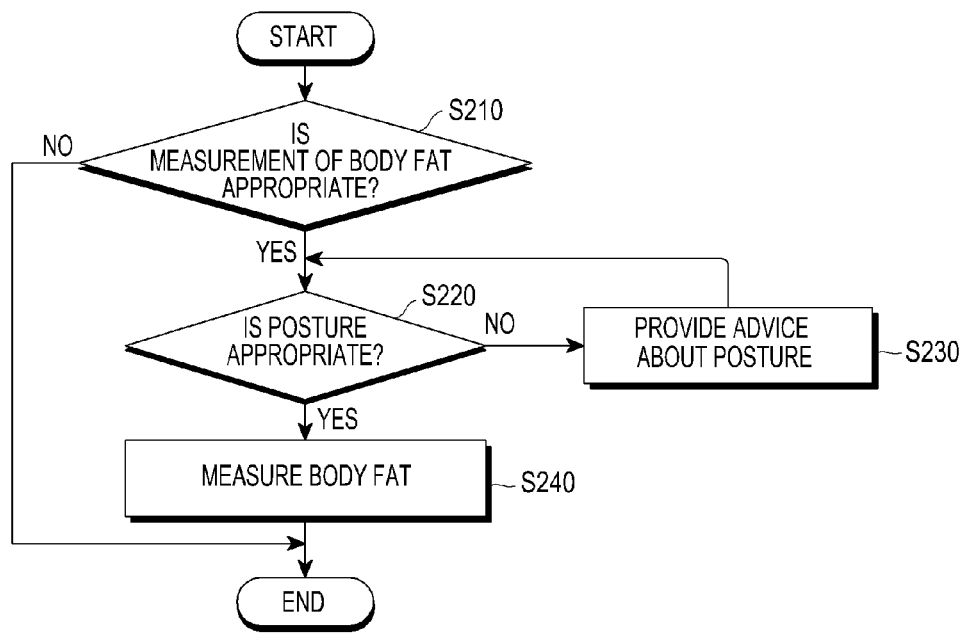
FIG. 16 illustrates a body fat measuring method according to an exemplary embodiment.

FIG. 16 illustrates a body fat measuring method according to an aspect of an exemplary embodiment of the present disclosure.

Operation S210 corresponds to an operation of determining whether it is appropriate to measure a body resistance. The controller 160 may be configured to check pacemaker information of a user profile, which is associated with whether a user uses a pacemaker, and stop the measurement of body fat in response to determining that the user uses the pacemaker. The process of measuring the body resistance causes a current of 500 μA and 50 kHz to flow through the user, and this may disturb the operation of the pacemaker and thus, fat measurement will not be performed on the user who has the pacemaker.

Operation S220 corresponds to an operation of determining whether a posture is appropriate. The controller 160 may recognize whether the joint of an arm of the user is bent using the first camera 261 that photographs the upper body of the user, and recognize whether the joint of a leg of the user is bent using the second camera 262 that photographs the lower body of the user.

Operation S230 corresponds to an operation of providing advice about a posture, the controller 160 may then provide advice through the speaker 143 and/or the display unit 130, so as to request the arm or the leg of the user to be straightened.

Operation S240 corresponds to an operation of measuring a body resistance. The body resistance sensor unit 155 may measure a body resistance of the user using the electrode unit 154. The body resistance sensor unit 155 may apply a current of a predetermined intensity to the user through the first electrode 251 and the fourth electrode 254, measure a voltage value between the second electrode 252 and the third electrode 253, and calculate a resistance value using a relationship (V=IR) among a voltage (V), a current (I), and a resistance (R). The body resistance sensor unit 155 may output the measured body resistance information (a voltage value or a calculated body resistance value), to the controller 160.

According to an aspect of an exemplary embodiment, body fat value may be obtained through a formula using the measured body resistance value and parameters such as a height, a weight, an age, and a sex. The formula may be obtained through a regression equation by comparing the body fat measured through the standard body fat measurement (specific gravity of water and Dual Energy X-ray Absorptiometry (DEXA)) and the parameters.

Alternatively, the controller 160 may calculate the body fat value by calculating a total body water (obtained by multiplying a constant and a value obtained by dividing the square of the height of the user by a body resistance value), obtaining an amount of protein and mineral through the general component ratio of the human body (water:protein:mineral:fat=55:20:20:5), and applying an equation of "body fat quantity=weight−(water+protein+mineral)". In addition to the body fat, other body components, such as a muscle mass, and the like may be further calculated. In particular, a current flows well through a part of the body that is high in water and thus, a resistance value is low. A current does not flow well through a part of the body that does not include much water and thus, a resistance value is high. Protein includes water when it is stored in the body, but fat is stored without water. Also, at least 70% of muscle is water. Accordingly, the muscle mass and the body component analysis may be performed using a degree of a current flow or a difference in body resistance value.

In addition, when measured values associated with health information of a user have changed over a threshold amount from previously measured values that are measured and stored in advance, advisory information may be provided to the user through a voice or an image.

Figures 17A, 17B, 17C:
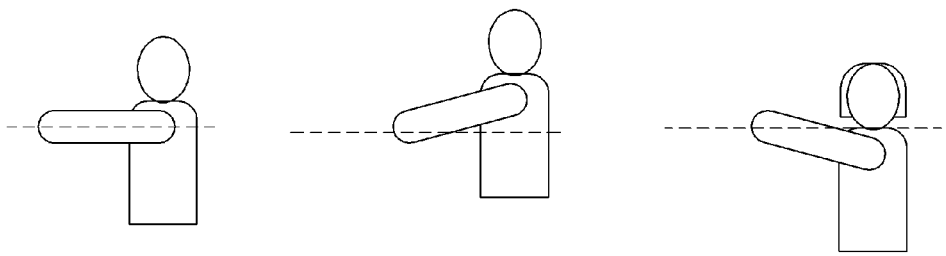
FIGS. 17A, 17B and 17C illustrate relationships between a body type and an angle of an arm.

FIGS. 17A-17C are diagrams illustrating relationships between a body type and an angle of an arm. The broken line indicates a vertical location of the electrode 154.

Referring to FIG. 17A, the user of the standard proportion is in a posture in which an arm and the body are at an angle of 90 degrees, and a measured body resistance value may be used as it is, for calculating body fat.

Referring to FIG. 17B, a user who is taller than the standard lowers an arm to hold a door (a portion where the electrode 154 is disposed) so as to open the refrigerator 100. In this instance, a body resistance value is measured to be lower and thus, when the measured body resistance value is used as it is, body fat value may be obtained inaccurately.

Referring to FIG. 17C, a user who is shorter than the standard raises an arm to hold a door (a portion where the electrode 154 is disposed) so as to open the refrigerator 100. In this instance, a body resistance value is measured to be higher and thus, when the measured body resistance value is used as it is, body fat value may be obtained inaccurately.

The controller 160 determines a user profile, including a calculated angle of a shoulder joint (an angle between an arm and the body) of the user, which is associated with a difference in height between the user and the standard proportion, and corrects the measured body resistance value using a predetermined body resistance correction algorithm.

Referring again to FIG. 6, operation S50 corresponds to an operation of providing a customized health service, and the controller 160 is configured to provide a user with a health service using an updated user profile.

The controller 160 may be configured to compare a measured biometric information value with a biometric information value stored before the measurement, and provide health information through at least one of the speaker 143 and the display unit 130 when a difference in biometric information is greater than or equal to a predetermined threshold value. For example, the controller 160 compares a measured muscle mass and a muscle mass stored before the measurement, and provides information associated with a change/variation of the muscle mass or information associated with a detected change in the health through at least one of the speaker 143 and the display unit 130 when a difference in muscle mass is greater than or equal to a predetermined threshold value.

The controller 160 may be configured to recognize eating habits of the user. The eating habits of the user include a time of using the refrigerator 100, a duration in which the refrigerator 100 is used, a frequency of use of the refrigerator 100, and/or the like. The controller 160 may analyze the eating habits of the user based on the eating habits information, and provide recommendations or advisories for proper eating habits. For example, the controller 160 may display advisory eating habits information on the display unit 130.

When a user frequently opens the refrigerator 100, the controller 160 may advise the user to execute an appropriate amount of exercise via an interoperated electronic device when the user is outside. For example, the controller 160 may transmit an advisory message for exercise to a portable phone of the user.

The controller 160 may be configured to distinguish a motion in which the user opens the refrigerator 100 based on a time of day, so as to distinguish whether the motion is for a meal or for a snack. When it is determined that the user opens the refrigerator 100 for a snack, the controller 160 may provide advice for preventing the same. For example, the controller 160 may display an advisory message on the display unit 130 or provide advice through sound using the speaker 143.

The controller 160 may lock a door of the refrigerator 100 to prevent children from excessive intake of instant food. For example, the controller 160 may transmit a message to preset contact information (for example, phone numbers of the parents) or may keep a door locked until the parents unlock the door through the communication unit 110.

The controller 160 may set user permissions for each of a plurality of doors included in the refrigerator 100, and a door lock device so that only an allowed user is able to unlock a corresponding door.

The controller 160 may obtain a Heart Rate Variability (HRV) based on electrocardiogram information, and analyze stress of a user based on the HRV. Based on the same, the controller 160 may advise the user to restrain intake of highly caffeinated food or beverages, which may cause excessive stress.

The controller 160 may also obtain a Heart Rate Variability (HRV) by measuring pulses when a body resistance is measured, and analyze stress of a user based on the HRV. Based on the same, the controller 160 may advise the user to restrain intake of highly caffeinated food or beverages which may cause excessive stress.

The controller 160 may share the living habits of the user with people around the user through the Internet or the like, and may recommend an appropriate food and life pattern for the user.

The controller 160 may determine how frequently the user intakes instant food obtained from the refrigerator 100 through data communication with a microwave including a biometric sensor (for example, an electrocardiogram sensor). For example, the controller 160 may receive a message from the microwave that includes biometric information which identifies a user, and the message may include information indicating a used-function associated with a microwave, used-time information, or the like.

The controller 160 may compare a type and amount of exercise executed by the user, obtained through data communication with an exercise machine including a biometric sensor (for example, electrocardiogram sensor), with eating habits associated with the use of the refrigerator 100, and advise the user how to have a healthy living habit.

The controller 160 may compare the eating habits of the user with the eating habits appropriate for the bowel habit of the user, obtained through data communication with a bidet in the bathroom including a biometric sensor (for example, electrocardiogram sensor), and based on the comparison, advise the user on healthy living habits.

The controller 160 may execute data communication with the weighing scale 156 including a biometric sensor (for example, an electrocardiogram sensor), so as to automatically update the weight of a user profile stored in the storage unit 120.

Figure 18:
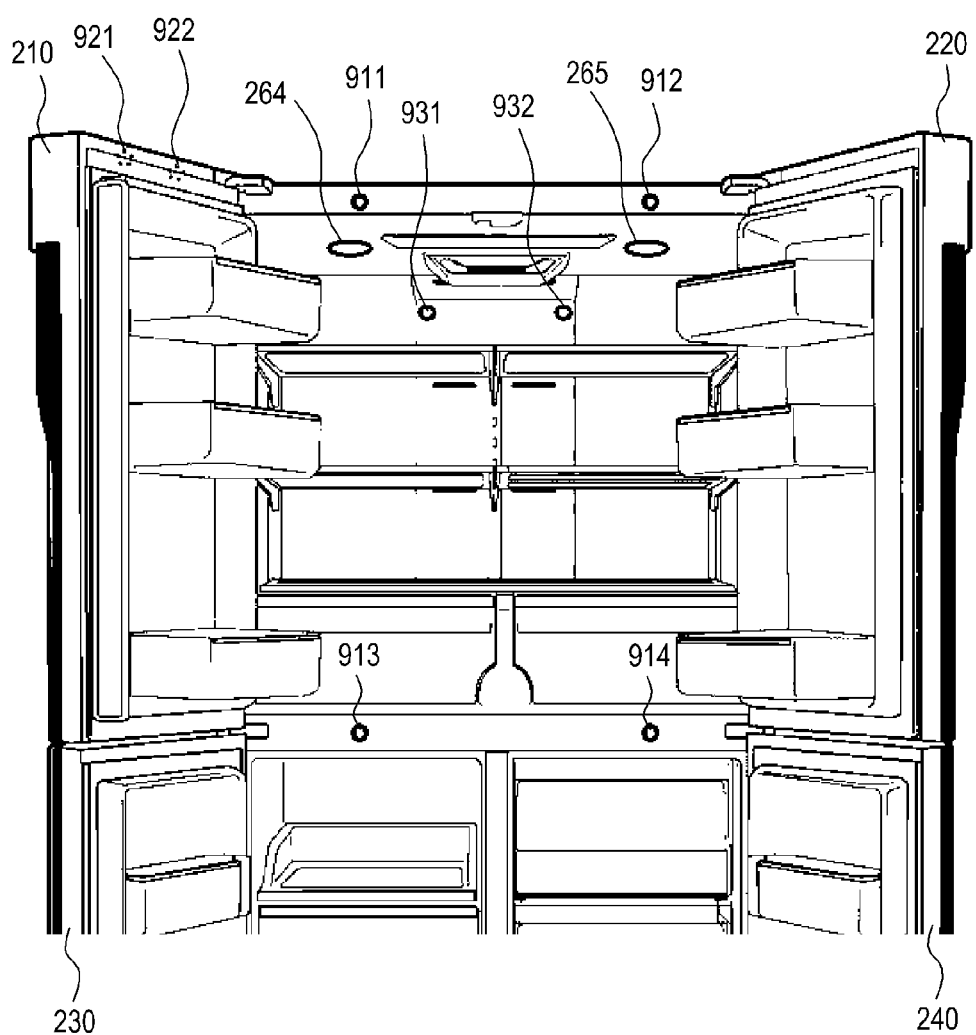
FIG. 18 illustrates sensors installed inside a refrigerator according to an exemplary embodiment.

FIG. 18 is a diagram illustrating sensors installed inside the refrigerator 100 according to an aspect of an exemplary embodiment of the present disclosure.

A first door sensor 911 for detecting an open/shut state of the first door 210 and a second door sensor 912 for detecting an open/shut state of the second door 220 may be disposed in the front side of the top side part of the main body of the refrigerator 100.

A third door sensor 913 for detecting an open/shut state of the third door 230 and a fourth door sensor 914 for detecting an open/shut state of the fourth door 240 may be disposed in the front side of the middle part of the main body of the refrigerator 100.

An external temperature sensor 921 and an external humidity sensor 922 may be disposed in the upper portion of the first door 210.

An internal temperature sensor 931 and an internal humidity sensor 932 may be disposed in the back side part of the main body of the refrigerator 100.

The first through fourth door sensors 911 through 914 each detects an open/shut state of a corresponding door and outputs the detected open/shut information of the corresponding door to the controller 160.

The external temperature sensor 921 is configured to measure the temperature outside the refrigerator 100, and output the measured outside temperature information to the controller 160. The external humidity sensor 922 is configured to measure the humidity outside the refrigerator 100, and output the measured outside humidity information to the controller 160.

The internal temperature sensor 931 is configured to measure the temperature inside the refrigerator 100, and output the measured inside temperature information to the controller 160. The internal humidity sensor 932 is configured to measure the humidity inside the refrigerator 100, and output the measured inside humidity information to the controller 160.

The fourth and fifth cameras 264 and 265 are disposed in the top side part of the main body of the refrigerator 100. The fourth and fifth cameras 264 and 265 are configured to photograph the inside of the refrigerator 100, and output the photographed image to the controller 160 or store the same in the storage unit 120. Although it is illustrated that the two cameras 264 and 265 are disposed for photographing a disposition of food inside the refrigerator 100, three or more cameras may be disposed in multiple locations for photographing everywhere inside the refrigerator 100.

Figure 19:
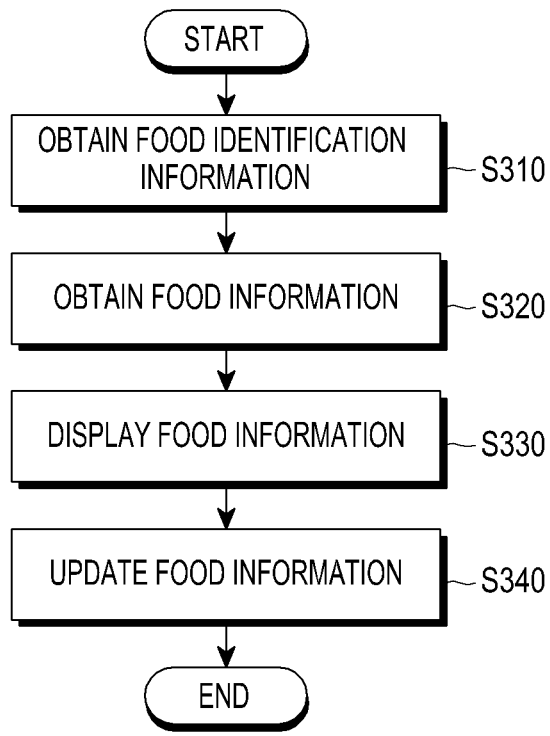
FIG. 19 is a flowchart illustrating a health service providing method according to an exemplary embodiment.

FIG. 19 is a flowchart illustrating a health service providing method according to an aspect of an exemplary embodiment of the present disclosure.

Operation S310 corresponds to an operation of obtaining food identification information. When a user puts food identification information, which is attached to food to be stored in the refrigerator 100, close to the scanner 157, the controller 160 may control the scanner 157 to recognize the food identification information. The controller 160 may receive the food identification information stored in an electronic device of the user via the communication unit 110. The controller 160 may receive the food identification information from the server 190.

Figure 20:
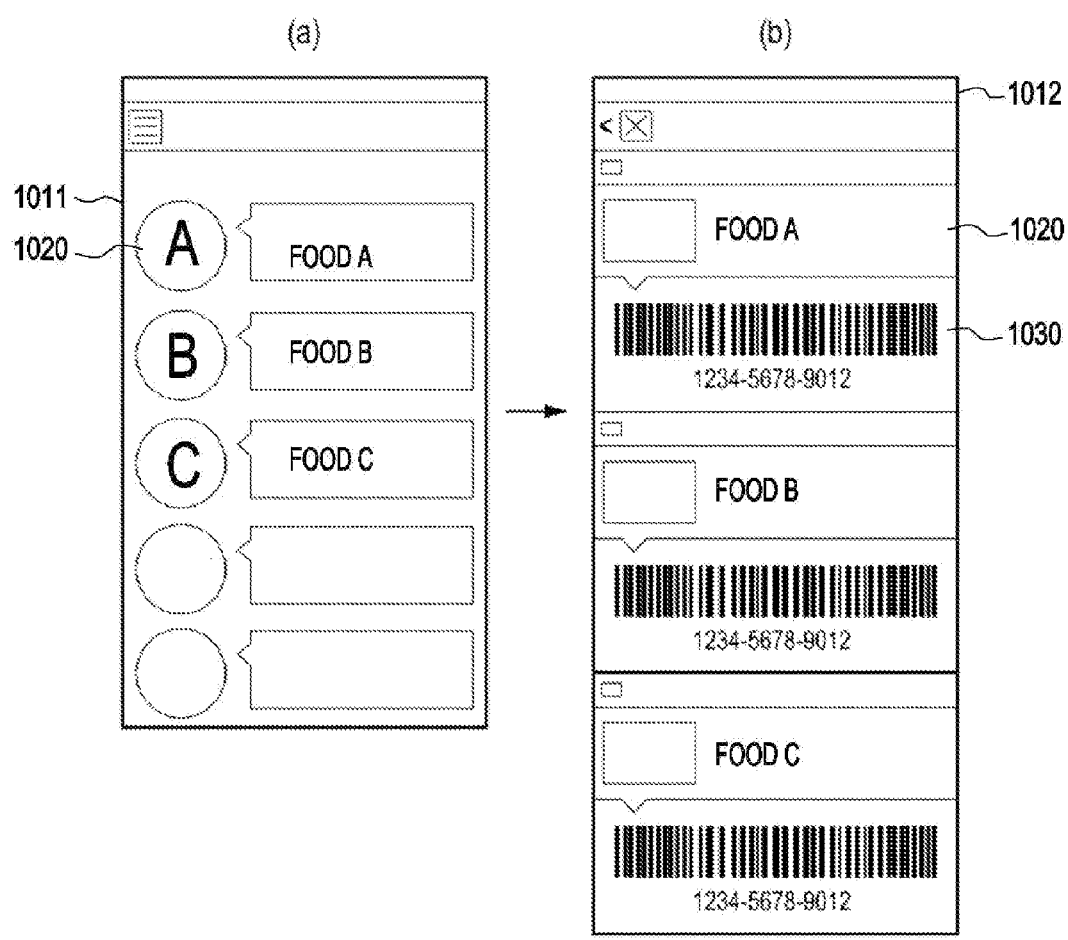
FIG. 20 is a diagram illustrating a process of receiving food identification information stored in an electronic device of a user according to an exemplary embodiment.

FIG. 20 is a diagram illustrating a process of receiving food identification information stored in an electronic device of a user according to an aspect of an exemplary embodiment of the present disclosure.

Referring to (a) of FIG. 20, the electronic device 181 may display food items 1020 that a user purchases, on a first screen 1011.

Referring to (b) of FIG. 20, the electronic device 181 may display barcodes 1030 of the food items 1020 that the user purchases according to the selection of the user, on a second screen 1012.

The user may enable the scanner 157 of the refrigerator 100 to scan the barcodes 1030 displayed on the electronic device, or may wirelessly or wiredly transmit the barcodes 1030 to the refrigerator 100.

Operation S320 corresponds to an operation of obtaining food information. The controller 160 may transmit food identification information to the server 190, and may receive food information (a name, a type, an external appearance image, weight, or a partial or whole combination thereof) from the server 190. Alternatively, the controller 160 may obtain food information corresponding to the food identification information using the Internet or the like. Alternatively, the controller 160 may receive food information from an electronic device of the user.

Operation S330 corresponds to an operation of displaying food information. The controller 160 may display an image of the inside of the refrigerator 100 and a food object, on the display unit 130.

Figure 21:
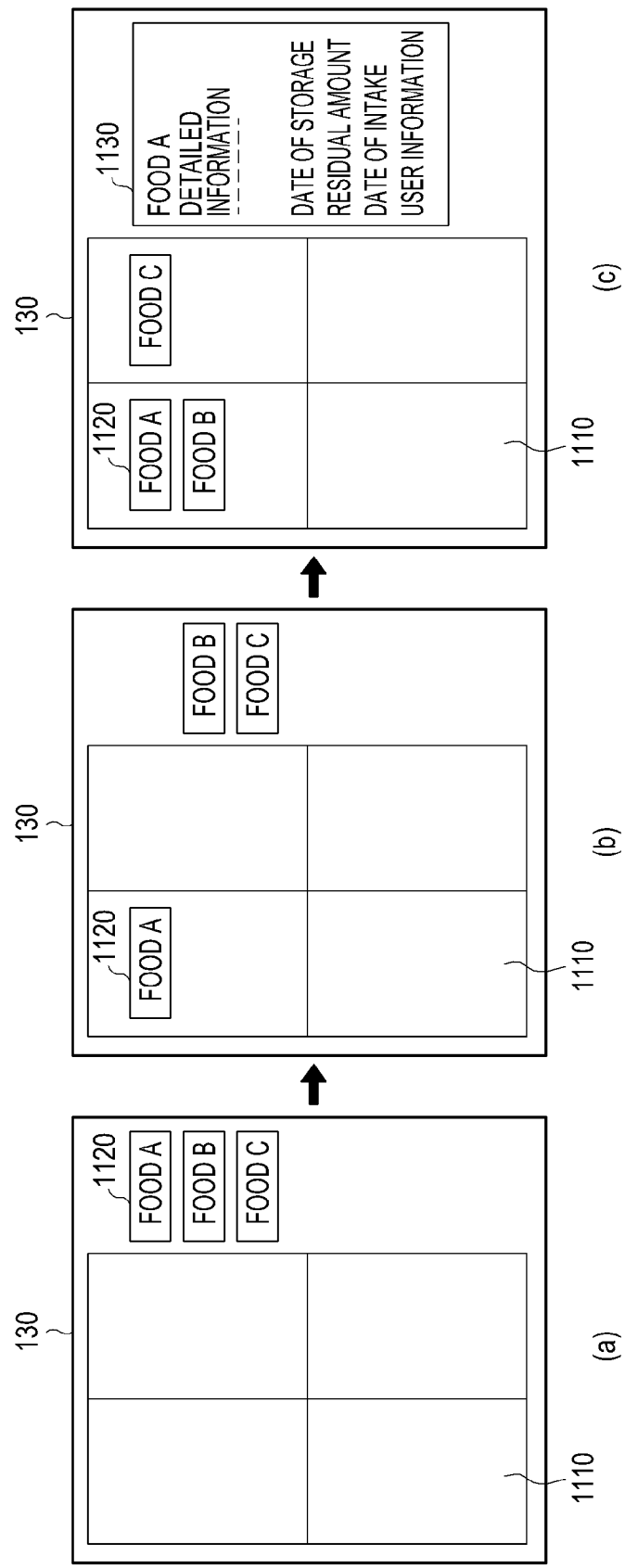
FIGS. 21 and 22 are diagrams illustrating a process of displaying food information according to an exemplary embodiment.
Figure 22:
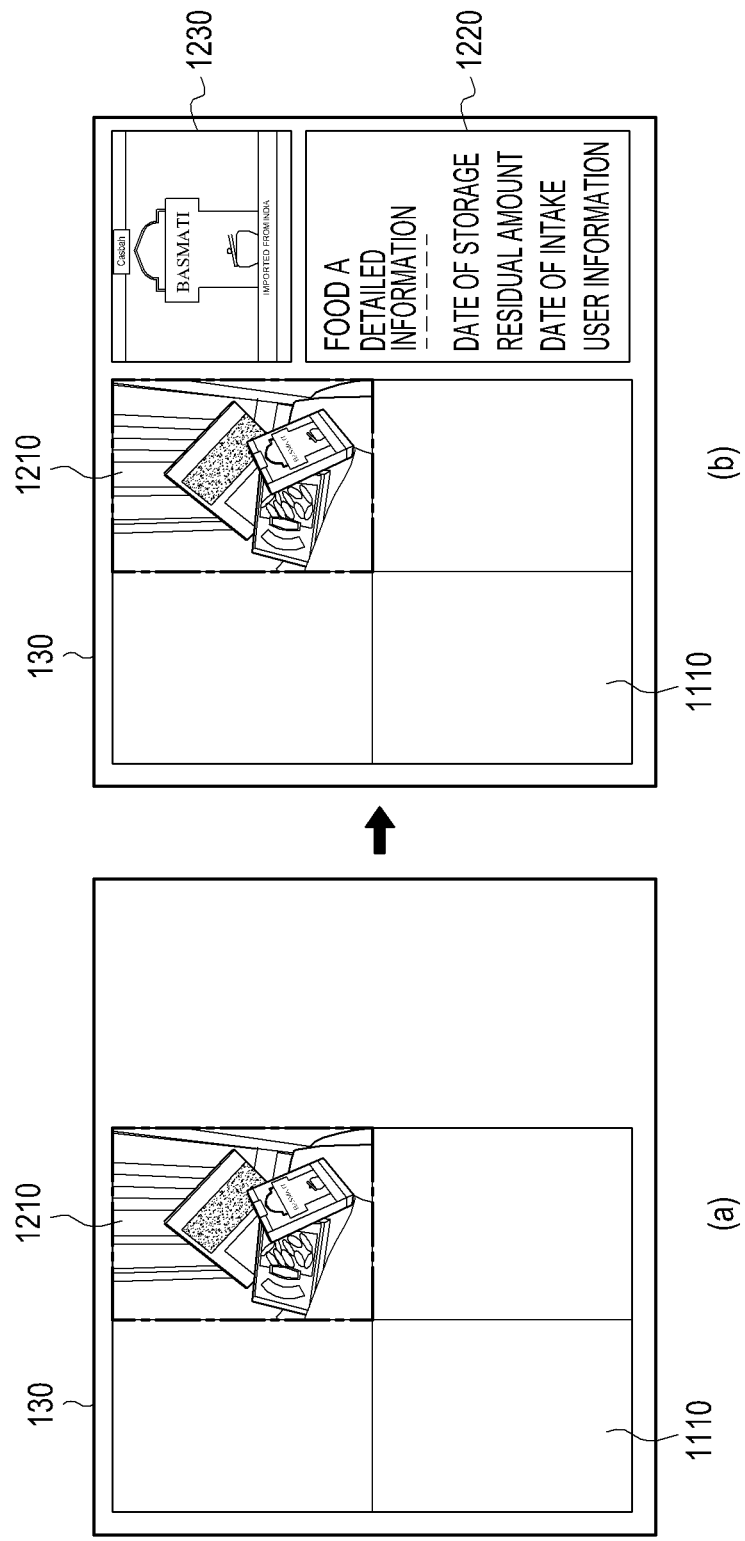

FIGS. 21 and 22 are diagrams illustrating a process of displaying food information according to an aspect of an exemplary embodiment of the present disclosure. Referring to (a) of FIG. 21, the controller 160 may be configured to display on the display unit 130, an internal space 1110 of the refrigerator 100 and a food object 1120. Although FIG. 21 schematically illustrates that the inside of the refrigerator 100 is divided into four parts, an image identical to the actual internal structure of the refrigerator 100 or the like may be displayed. Referring to (b) of FIG. 21, a user moves the food object 1120 to a desired location of the internal space 1110 of the refrigerator 100, through a drag gesture or the like.

Referring to (c) of FIG. 21, when a user selects a food object, the controller 160 may display detailed information 1130 of the food object 1120 (a date of storage, a residual amount, a date of intake, user information associated with a user who intakes food, or a partial or whole combination thereof), on the display unit 130.

Referring to (a) of FIG. 22, the controller 160 may be configured to display on the display unit 130, the internal space 1110 of the refrigerator 100. An exemplary image 1210 of a multi-purpose drawer inside the refrigerator 100, photographed by a camera (for example, a fourth or fifth camera) is illustrated. Although a user does not necessarily input information (a location, food identification information, and the like) associated with food located inside the refrigerator 100, the controller 160 may automatically recognize food from the image 1210 of the inside of the refrigerator 100 photographed by a camera based on the food information stored in the storage unit 120.

The controller 160 may recognize food identical to the food information stored in the storage unit 120, from the image of the inside of the refrigerator 100 through an algorithm such as Scale Invariant Feature Transform (SIFT), Speeded Up Robust Features (SURF), or the like.

Referring to (b) of FIG. 22, when a user selects a subject corresponding to the food recognized from the image 1210 of the inside of the refrigerator 100, the controller 160 may display detailed information 1220 of the food (a cover image 1230, a date of storage, a residual amount, a date of intake, user information associated with a user who intakes food, and the like), on the display unit 130. Alternatively, the controller 160 may automatically display, on the display unit 130, information corresponding to the food recognized from the image 1210 of the inside of the refrigerator 100. Alternatively, the controller 160 may transmit the image 1210 of the inside of the refrigerator 100 to the server 190, may receive detailed information 1220 of the food recognized from the image 1210 by the server 190, and may display, on the display unit 130, the detailed information 1220 received from the the server 190.

Operation S340 corresponds to an operation of updating food information. The controller 160 may update food information stored in the storage unit 120, based on a user input (correcting a residual amount or the like).

It will be appreciated that the embodiments of the present disclosure may be implemented in software, hardware, or a combination thereof. For example, in the refrigerator illustrated in FIG. 1, components such as the storage unit, the communication unit, and the controller may be implemented as devices, respectively. Any such software may be stored, for example, in a volatile or non-volatile storage device such as a ROM, a memory such as a RAM, a memory chip, a memory device, or a memory IC, or a recordable optical or magnetic medium such as a CD, a DVD, a magnetic disk, a magnetic tape, regardless of its ability to be erased or its ability to be re-recorded, or the like. It will also be appreciated that the memory included in the refrigerator is one example of machine-readable devices suitable for storing a program including instructions that are executed by a processor device to thereby implement embodiments of the present disclosure. Accordingly, the present disclosure includes a program that includes a code for implementing an apparatus or a method of the present disclosure, and a machine-readable storage medium that stores such a program. Further, the program may be electronically transferred by a predetermined medium such as a communication signal transferred through a wired or wireless connection, and the present disclosure appropriately includes equivalents of the program.

Further, the refrigerator may receive the program from a program providing apparatus connected to the device wirelessly or through a wire and store the received program. The program providing apparatus may include a program including instructions allowing the refrigerator to perform the method of providing a health service, a memory for storing information required for the health service providing method, a communication unit for performing wired or wireless communication with the refrigerator, and a controller for transmitting the corresponding program to the refrigerator at the request of the refrigerator or automatically.

While one or more exemplary embodiments have been described with reference to the figures, it will be understood by those of ordinary skill in the art that various modifications can be made without departing from the spirit and scope of the present disclosure. Accordingly, the scope of the present disclosure shall not be determined by the above-described embodiments, and is to be determined by the following claims and their equivalents.

What is claimed is:

1. A method of providing a health service through a refrigerator, the method comprising:
    obtaining first biometric information of a user using at least one sensor unit of the refrigerator;
    searching a storage unit of the refrigerator for a user profile including biometric information corresponding to the obtained first biometric information;
    determining whether the user is an object for measuring second biometric information based on the searched user profile;
    in response to the user being the object, obtaining at least one image of the user using at least one camera of the refrigerator;
    determining whether a posture of the user is appropriate for measuring the second biometric information, based on the at least one image;
    when determining that the posture is inappropriate, providing advice about a predetermined posture;
    when determining that the posture is appropriate, measuring the second biometric information of the user; and
    modifying a value of the measured second biometric information based on at least one of the user profile and the at least one image.

2. The method of claim 1, wherein the obtained first biometric information is an electrocardiogram of the user.

3. The method of claim 2, wherein the electrocardiogram of the user is identification information from which a predetermined common component is removed.

4. The method of claim 1, further comprising:
determining whether to update the user profile, based on a point in time of registration of information included in the user profile.

5. The method of claim 1, further comprising:
measuring a body resistance of the user when it is determined to be appropriate to measure the body resistance; and
determining body fat of the user based on the body resistance.

6. The method of claim 1, wherein the determining whether the user is the object comprises determining that the user is not the object for measuring second biometric information and measuring a body resistance of the user is inappropriate, in response to the user profile including information indicating that a pacemaker is used.

7. The method of claim 1, wherein the obtained first biometric information includes facial recognition information of the user, iris recognition information, or fingerprint recognition information.

8. The method of claim 1, further comprising:
receiving device information of an electronic device adjacent to the refrigerator,
wherein the received device information is used for searching for the user profile.

9. A non-transitory machine-readable storage medium that records a program for implementing a method of providing a health service through a refrigerator, the method comprising:
obtaining first biometric information of a user using at least one sensor unit of the refrigerator;
searching a storage unit of the refrigerator for a user profile including biometric information corresponding to the obtained first biometric information;
determining whether the user is an object for measuring second biometric information based on the searched user profile;
in response to the user being the object, obtaining at least one image of the user using at least one camera of the refrigerator;
determining whether a posture of the user is appropriate for measuring the second biometric information, based on the at least one image;
when determining that the posture is inappropriate, providing advice about a predetermined posture;
when determining that the posture is appropriate, measuring the second biometric information of the user; and
modifying a value of the measured second biometric information based on at least one of the user profile and the at least one image.

10. A refrigerator that provides a health service, the refrigerator comprising:
a storage unit;
at least one sensor unit;
at least one camera;
a controller configured to:
obtain first biometric information of a user using the at least one sensor unit;
search the storage unit for a user profile including biometric information corresponding to the obtained first biometric information;
determine whether the user is an object for measuring second biometric information based on the searched user profile;
in response to the user being the object, obtain at least one image of the user using the at least one camera;
determine whether a posture of the user is appropriate for measuring the second biometric information, based on the at least one image;
when determining that the posture is inappropriate, provide advice about a predetermined posture;
when determining that the posture is appropriate, measure the second biometric information of the user; and
modify a value of the measured second biometric information based on at least one of the user profile and the at least one image.

11. The refrigerator of claim 10, wherein the at least one sensor unit includes an electrocardiogram sensor unit configured to determine an electrocardiogram of the user using an electrode; and
wherein the obtained first biometric information is the determined electrocardiogram of the user.

12. The refrigerator of claim 11, wherein the controller is further configured to search for the user profile using identification information obtained by removing a predetermined common component from the determined electrocardiogram of the user.

13. The refrigerator of claim 10, wherein the controller is further configured to determine whether to update the user profile based on a point in time of registration of information included in the user profile.

14. The refrigerator of claim 10, further comprising:
a body resistance sensor unit,
wherein the controller is further configured to measure a body resistance of the user using the body resistance sensor unit in response to determining that it is appropriate to measure the body resistance of the user, and calculate body fat of the user based on the body resistance.

15. The refrigerator of claim 10, wherein, the controller is further configured to determine that the user is not the object for measuring second biometric information and measuring a body resistance of the user is inappropriate, in response to the user profile containing information indicating that a pacemaker is used.

16. The refrigerator of claim 10, wherein the at least one sensor unit includes at least one of a camera configured to recognize a face of the user, an iris sensor configured to recognize an iris of the user, a fingerprint sensor configured to recognize a fingerprint of the user, and a communication unit configured to receive device information of an electronic device adjacent to the refrigerator.

* * * * *